(12) United States Patent
Burns et al.

(10) Patent No.: US 7,144,920 B2
(45) Date of Patent: *Dec. 5, 2006

(54) POLYAMINE ANALOGS THAT ACTIVATE ANTIZYME FRAMESHIFTING

(75) Inventors: Mark R. Burns, Shoreline, WA (US); Gerard F. Graminski, Shoreline, WA (US)

(73) Assignee: MediQuest Therapeutics, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/810,649

(22) Filed: Mar. 29, 2004

(65) Prior Publication Data

US 2004/0209926 A1    Oct. 21, 2004

Related U.S. Application Data

(63) Continuation-in-part of application No. 10/251,819, filed on Sep. 23, 2002, now Pat. No. 6,914,079.

(51) Int. Cl.
   A61K 31/135    (2006.01)
   C07D 211/18    (2006.01)

(52) U.S. Cl. ..................... 514/649; 564/336

(58) Field of Classification Search ............. 564/336; 514/649

See application file for complete search history.

(56) References Cited

U.S. PATENT DOCUMENTS

| | | | |
|---|---|---|---|
| 3,755,455 A | 8/1973 | Houlihan | |
| 4,605,765 A | 8/1986 | Miyamoto et al. | |
| 4,720,789 A | 1/1988 | Shander | |
| 5,648,394 A | 7/1997 | Boxall et al. | |
| 6,001,824 A | 12/1999 | Nakanishi et al. | |
| 2004/0058954 A1 | 3/2004 | Burns et al. | |

FOREIGN PATENT DOCUMENTS

| | | |
|---|---|---|
| EP | 0 645 370 A1 | 3/1995 |
| WO | WO-96/22982 | 8/1996 |
| WO | WO-00/46187 | 8/2000 |
| WO | WO-00/46187 A3 | 8/2000 |
| WO | WO-01/92218 A2 | 12/2001 |

OTHER PUBLICATIONS

Graminski Gerard Francis et al., *Polyamine analogs that regulate antizyme frameshifting*, vol. 16, No. 4, Mar. 20, 2002, XP009043569, p. A537.

Burns, Mark R. et al., *Induction of Apoptosis by Aryl-Substituted Diamines: Role of Aromatic Group Substituents and Distance Between Nitrogens* Bioorganic & Medicinal Chemistry Letters vol. 12, No. 9, May 6, 2002, pp. 1263-1267, XP002316301.

Kent D. Stewart et al, Survey of the DNA Binding Properties of Natural and Synthetic Polyamino Compounds, Journal of Physical Organic Chemistry, vol. 5, 461-466 (1992).

(Continued)

*Primary Examiner*—Rita J. Desai
(74) *Attorney, Agent, or Firm*—Connolly, Bove, Lodge & Hutz, LLP

(57) ABSTRACT

Novel polyamines, their synthesis and use in pharmacological, cosmetic or agricultural applications are provided. The polyamines induce antizyme production which in turn down regulates both the production of polyamines by omithine decarboxylase (ODC) and the transport of polyamines by its corresponding polyamine transporter. These compounds will preferably enter the cell independent of the polyamine transporter. As drugs, these compounds are used to treat any disease associated with cellular proliferation including but not limited to cancer.

9 Claims, 12 Drawing Sheets

OTHER PUBLICATIONS

Laurence Covassin et al, "Synthesis of Spermidine and Norspermidine Dimers as High Affinity Polyamine Transport Inhibitors", Bioorganic & Medicinal & Chemistry Letters, vol. 9, 1999, pp. 1710-1714.

Joseph Satriano et al., "Agmatine Suppresses Proliferation by Frameshift Induction of Antizyme and Attenuation of Cellular Polyamine Levels", The Journal of Biological Chemistry, 1998, vol. 273, No. 25, pp. 15313-15316.

John L. A. Mitchell et al., "Antizyme Induction by Polyamine Analogues as a Factor of Cell Growth Inhibition", Biochemical Society, 2002, vol. 366 pp. 663-671.

Michael T. Howard et al., "Cell Culture Analysis of the Regulatory Frameshift Even Required for the Expression of Mammalian Antizymes", Blackwell Science Limited, Gene to Cells, 2001, vol. 6, pp. 937-941.

Satoshi Iwata et al., "Anti-Tumor Activity of Antizyme Which Targets the Ornithine Decarboxylase (ODC) Required for Cell Growth and Transformation", Oncogeno 18, 1999, 99. 164-172.

William Wells, "How the Prostate Restrains Cancer Cell", The American Society for Cell Biology 2000, Dec. 12, 2000.

John L. Mitchell et al., "Osmotic Stress Induces Variation in Cellular Levels of Ornithine Decarboxylase-Antizyme", Biochemical Society, 1998, vol. 329, 99. 453-459.

Rebecca P. Schall et al., "Difluoromethylornithine (DFMO) Arrests Murine CTL Development in the Late, Pre-Effector Stage", Immunopharmacology, vol. 21, 1991, pp. 129-144.

Yoshio Sato, "The Hair Cycle and Its Control Mechanism", Department of Dermatology, Niigata University School of Medicine. Niigata, Japan, pp. 3-13.

Charles M. Henley, "Kanamycin Depletes Cochlear Polymines in the Developing Rat", The American Academy of Otolaryngology—Head and Neck Surgery Foundation, Inc., vol. 110. No. 1, 1994, pp. 103-109.

James A. Crowell et al. "Chronic Toxicity Studies of the Potential Cancer Preventative 2-(Difluoromethyl)-DL-Ornithine[1]", Fundamental and Applied Toxicology, vol. 22, pp. 341-354.

Andrew G. Messenger, "The Control of Hair Growth: An Overview", The Society for Investigative Dermatology, Inc., The Journal Investigative Dermatology, 1993, vol. 101, No. 1, Supplement, pp. 48-93.

A. A. Panteleyov et al., "Ornithine Decarboxylase Transgenic Mice as a Model for Human Atrichia with Papular Lesions", Experimental Dermatology, 2000, pp. 146-151.

Philip I. Hynd et al., "Inhibition of Polyamine Synthesis Alters Hair Follicle Function and Fiber Composition", The Society for Investigative Dermatology, Inc., The Journal of Investigative Dermatology, 1996, pp. 249-253.

J. Pepin et al., "Difluoromethylorinthine for Arseno-Resistant Trypanosoma Brucei Gambiense Sleeping Sickness", The Lancet, Dec. 19, 1987, pp. 1431-1433.

Deane M. Morrison et al., "Ornithine Decarboxylase in Rat Skin", The Journal of Investigative Dermatology, 1978, vol. 70, No. 6, pp. 309-313.

Tokihiko Shimada et al., "Correction of Ornithine Transcarbamylase (OTC) Deficiency in SPF-ASH Mice by Introduction of Rat OTC Gene", Federation of European Biochemical Societies, Feb. 1991, vol. 279, No. 2, pp. 198-200.

Guido Grentzmann et al., "A Dual-Luciferase Reporter System for Studying Recoding Signals", RNA Society, 1998, vol. 4, pp. 479-486.

M. Bouclier et al., "Induction of Ornithine Decarboxylase Activity in Hairless Rat Epidermis as a Pharmacological Model: Validation of the Animal Model", Laboratory Animals, 1987, vol. 21, pp. 233-240.

Michelle J. Nancarrow et al., "Dynamic Expression of Ornithine Decarboxylase in Hair Growth", Mechanisms of Development, 1999, vol. 84, pp. 161-164.

Senya Matsufuji et al., "Autoregulatory Frameshifting in Decoding Mammalian Ornithine Decarboxylase Antizyme", Cell, Jan. 13, 1995, vol. 80, pp. 51-60.

Elisabeth Probst et al., "Ornithine Decarboxylase Activity in Relation to DNA Synthesis in Mouse Interfollicular Epidermis and Hair Follicles", Biochimica et Biophysica Acta, 1975, vol. 407, pp. 147-157.

John L. A. Mitchell et al., "Overproduction of Stable Ornithine Decarboxylase and Antizyme in the Difluoromethylornithine-Resistant Cell Line DH23B", Biochemical Society, 1996, vol. 317, pp. 811-816.

Katja Kankare et al., "Structure, Organization and Expression of the Mouse Ornithine Decarboxylase Antizyme Gene", Biochemical Society, 1997, vol. 324, pp. 807-813.

Philip Coffino, "Antizyme, A Mediator of Ubiquitin-Independent Proteasomal Degradation", Biochimie, 2001 vol. 83, pp. 319-323.

Louis Megosh et al., "Increased Frequency of Spontaneous Skin Tumors in Transgenic Mice Which Overexpress Ornithin Decarboxylase", Cancer Research, Oct. 1, 1995, vol. 55, pp. 4205-4209.

David J. Feith et al., "Targeted Antizyme Expression in the Skin of Transgenic Mice Reduces Tumor Promoter Induction o Ornithine Decarboxylase and Decreases Sensitivity to Chemical Carcinogenesis", Cancer Research, Aug. 15, 2001, vol. 61, pp. 6073-6081.

Satoshi Iwata et al., "Anti-Tumor Activity of Antizyme Which Target the Ornithine Decarboxylase (ODC) Requiared for Cell Growth and Transformation", Oncogene, 1999, vol. 18, pp. 165-172.

Yasuko Murakami et al, "Forced Expression of Antizyme Abolishes Ornithine Decarboxylase Activity, Suppresses Cellular Levels of Polyamines and Inhibits Cell Growth", Biochemical Society, 1994, vol. 304, pp. 183-187.

Marko Pietila et al., "Relation of Skin Polyamines to the Hairless Phenotype in Transgenic Mice Overexpressing Spermidine/Spermine $N^1$—Acetyltransferease", The Journal of Investigative Dermatology, A. I. Virtanen Institute for Molecular Science, May 5, 2001, vol. 116, No. 5, pp. 801-805.

Takanori Tsuji et al., "Induction of Epithelial Differentation and DNA Demethylation in Hamster Malignant Oral Keratinocyte by Ornithine Decarboxylase Antizyme", Oncoogene, 2001, vol. 20, pp. 24-33.

Shin-ichi Hayashi et al., "Ornithin Decarboxylase Antizyme: A Novel Type of Regulatory Protein", TIBS, Jan. 1996, vol. 21, pp. 27-30.

Philip Coffino, "Regulation of Cellular Polyamines by Antizyme", Department of Microbiology and Immunology and Department of Medicine, University of California, San Francisco, Mar. 2001, vol. 2, pp. 188-194.

Aaron Ciechanover et al., "The Ubiquitin-Proteasome Proteolytic Pathway", Cell, Oct. 7, 1994, vol. 79, pp. 13-21.

Xianqiang Li et al., "Distinct Domains of Antizyme Required for Binding and Proteolysis of Ornithine Decarboxylase", Molecular and Cellular Biology, Jan. 1994, vol. 14, No. 1, pp. 87-92.

Xianqiang Li et al., "Regulated Degradation of Ornithine Decarboxylase Requires Interaction with the Polyamne-Inducible Protein Antizyme", Molecular and Cellular Biology, Aug. 1992, vol. 12, No. 8, pp. 3556-3562.

Zippi Bercovich et al., "Degradation of Ornithine Decarboxylase in Reticulocyte Lysate is ATP-Dependent but Ubiquitin-Independent", The Journal of Biology Chemistry, Sep. 25, 1989, vol. 264, No. 27, pp. 15949-15952.

Yasuko Murakami et al, "Ornithine Decarboxylase is Degraded by the 26S Proteasome Without Ubiquitination", Nature, Dec. 10, 1992, vol. 360, pp. 597-599.

Fuminori Tokunaga et al., "ATP-and Antizyme-Dependent Endoproteolysis of Ornithine Decarboxylase to Oligopeptides by the 26 S Proteasome", The Journal of Biological Chemistry, Jul. 1, 1994, vol. 269, No. 26, pp. 17382-17385.

Nora Moyano et al., "Inhibition of Ornithine Decarboxylase by the Isomers of 1,4-Dimethylputrescine", J. Med. Chem., 1990, vol. 33, pp. 1969-1974.

R. F. Gesteland et al., "Recoding: Reprogrammed Genetic Decoding", Science, Sep. 18, 1992, vol. 257, pp. 1640-1641.

Deborah A. Thomas et al., "Growth Inhibition of a Rat Colon Tumor by L-Canavanine", Cancer Research, Jun. 1986, vol. 46, pp. 2898-2903.

Tse-I Lin et al., "Different Modes of Inhibition by Adamantane Amine Derivatives and Natural Polyamines of the Functionally Reconstituted Influenze Virus M2 Proton Channel Protein", Journal of General Virology, 1997, vol. 78, pp. 767-774.

Svetiana Ivanova et al., "Cerebral Ischemia Enhances Polyamine Oxidation: Identification of Enzymatically Formed 3-Aminopropanal as an Endogenous Mediator of Neuronal and Glial Cell Death" J. Exp. Med., Jul. 20, 1998, vol. 188, No. 2, pp. 327-340.

S. Bettuzzi et al., "Coordinate Changes of Polyamine Metabolism Regulatory Proteins During the Cell Cycle of Normal Human Dermal Fibroblasts", Federation of European Biochemical Societies, 1999, Letter 446, pp. 18-22.

Claudio Stefanelli et al., "Spermine Causes Caspase Activation in Leukaemia Cells", Federation of European Biochemical Societies, 1998, Letters 437, pp. 233-236.

Gerardo Aizencang et al., "Antiproliferative Effects of $N^1$, $N^4$-Dibenzyluputrescine in Human and Rodent Tumor Cells", Cellular and Molecular Biology, 1998, vol. 44, No. 4, pp. 615-625.

Francesca Scorcioni et al., "Manipulation of the Expression of Regulatory Genes of Polyamine Metabolism Results in Specific Alterations of the Cell-Cycle Progression", Biochem J., 2001, vol. 354, pp. 217-223.

Suvlkki Suppola et al., "Concurrent Overexpression of Ornithine Decarboxylase and Spermidine/Spermine N1-Acetyltransferease Further Accelerates the Catabolism of Hepatic Polyamines in Transgenic Mice", Biochem J. 2001, vol. 358, pp. 343-348.

Xianqiang Li et al., "Degradation of Ornithine Decarboxylase: Exposure of the C-Terminal Target by a Polyamine-Inducible Inhibitory Protein", Molecular and Cellular Biology, Apr. 1993, vol. 13, No. 4, pp. 2377-2383.

John L. A. Mitchell et al., "Feedback Repression of Polyamine Transport is Medicated by Antizyme in Mammalian Tissue-Culture Cells", Biochem J., 1994, vol. 299, pp. 19-22.

Kaori Sakata et al., "Identification of Regulatory Region of Antizyme Necessary for the Negative Regulation of Polyamine Transport", Biochemical and Biophysical Research Communications, 1997, vol. 238, pp. 415-419.

Toshizkazu Suzuki et al., "Antizyme Protects Agains Abnormal Accumulation and Toxicity of Polyamines in Ornithine Decarboxylase-Overproducing Cells", Proc. Natl. Acad. Sci., Sep. 1994, vol. 91, pp. 8930-8934.

Chang Zhu et al., "Antizyme2 is a Negative Regulator of Ornithine Decarboxylase and Polyamine Transport", The Journal of Biological Chemistry, Sep. 10, 1999, vol. 274, No. 37, pp. 26425-26430.

Kaori Sakata et al., "Properties of a Polyamine Transporter Regulated by Antizyme", Biochem J. 2000, vol. 347, pp. 297-303.

Masaharu Takigawa et al., "Inhibition of Mouse Skin Tumor Promotion and of Promoter-Stimulated Epidermal Polyamine Biosymthesis by Difluoromethylornithine", Cancer Research, Aug. 1983, vol. 43, pp. 3732-3738.

Alejandor Peralta Soler et al., "Modulation of Murine Hair Follicle Function by Alterations in Ornithine Decarboxylase Activity", The Journal of Investigative Dermatology, May 5, 1996, vol. 106, No. 5, pp. 1108-1113.

Misty L. McWilliams et al., "Characterization of the Ototoxicity of Difluoromethylornithine and its Enantiomers", Toxicological Sciences, 2000, vol. 56, pp. 124-132.

C. S. Harmon et al., "Hair Fibre Production by Human Hair Follicles in Whole-Organ Culture", British Journal of Dermatology, 1994, vol. 130, pp. 415-423.

Michael P. Phllpott et al., "Human Hair Growth In Vitro: A Model for the Study of Hair Follicle Biology", Journal of Dermatological Science, 1994, vol. 7 (Suppl), pp. S55-S72.

Tokihiko Shimada et al., "Correction fo Ornithine Transcarbamylase (OTC) Dificiency in SPF-ASH Mice by Introduction of Rat OTC Gene", Federation of European Biochemical Societies, Feb. 1991, vol. 279, No. 2, pp. 198-200.

John L. A. Mitchell et al., "Conformational Changes in Ornithine Decarboxylase Enable Recognition by Antizyme", Biochimica et Biophysica Acta, 1990, vol. 1037, pp. 115-121.

Ivaylo P. Ivanov et al. "Discovery of a Spermatogenesis Stage-Specific Ornithine Decarboxylase Antizyme: Antizyme 3", PNAS, Apr. 25, 2000, vol. 97, No. 9, pp. 4808-4813.

Philip Coffino, "Polyamines in Spermiogenesis: Not Now, Darling", PNAS, Apr. 25, 2000, vol. 97, No. 9, pp. 4421-4423.

Scott C. Thomson et al., "Ornithine Decarboxylase, Kidney Size, and the Tubular Hypothesis fo Glomerular Hyperfiltration in Experimental Diabetes", The Journal of Clinical Investigation, Jan. 2001, vol. 107, No. 2, pp. 217-224.

Yasuko Murakami et al., "ATP-Dependent Inactivation and Sequestration of Ornithine Decarboxylase by the 26S Proteasome are Prerequisites for Degradation", Molecular and Cellular Biology, Oct. 1999, vol. 19, No. 10, pp. 7216-7227.

Andrew D. Kern et al., "Structure of Mammalian Ornithine Decarboxylase at 1.6A Resolution: Stereochemical Implication of PLP-Dependent Amino Acid Decarboxylases", Research Article, Structure 1999, vol. 7, No. 5, pp. 567-581.

Sary Ben-Shahar et al., "26 s Proteasome-Mediated Production of an Authentic Major Histocompatibility Class I-Restricted Epitope from an Intact Protein Substrate", The Journal of Biological Chemistry, vol. 274, Jul. 30, 1999, No. 31, pp. 21963-21972.

John R. Lakanen et al., " $\alpha$ -Methyl Polyamines: Metabolically Stable Spermidine and Spermine Mimics Capable of Supporting Growth in Cells Depleted of Polyamines", J. Med. Chem., 1992, No. 35, pp. 724-734.

C. Aubel et al.., "Antizyme-Dependent and Independent Mechanisms are Responsible for Increased Spermidine Transport in Amino Acid-Restricted Human Cancer Cells", Biochemical and Biophysical Research Communications, 1999, vol. 256, No. 3, pp. 646-651.

John V. Fleming et al. "Amino-and Carboxy-Terminal Pest Domains Mediate Gastrin Stabilization of Rat L-Histidine Decarboxylase Isoforms" Molecular and Celluar Biology, Jul. 2000, vol. 20, No. 13, pp. 4932-4947.

Manas K. Chattopadhyay et al. "Antizyme Regulates the Degradation of Ornithine Decarboxylase in Fission Yeast Schizosaccaraomyces Pombe", The Journal of Biological Chemistry, Jun. 2001, vol. 276, No. 24, pp. 21235-21241.

Yasuko Murakami et al., "Destabilization of Ornithine decarboxylase by Transfected Antizyme Gene Expression in Hepatoma Tissue Culture Cells", The Journal of Biological Chemistry, Jul. 5, 1992, vol. 267, No. 19, pp. 13138-13141.

Jonas Nilsson et al., "Antizyme Inhibitor is Rapidly Induced in Growth-Stimulated Mouse Fibroblasts and Releases Ornithine Decarboxylase from Antizyme Suppression", Biochem. J. 2000, vol. 346, pp. 699-704.

Ivaylo P. Ivanov et al., "Conservation of Polyamine Regulation by Translational Frameshifting from Yeast to Mammals", European Molecular Biology Organization, 2000, pp. 1907-1917.

Stewart, K.D. et al. Survey of the DNA Binding Properties of Natural and Synthetic Polyamino Compounds, Journal of Physical Organic Chemistry, vol. 5, 1992, pp. 461-466.

| ID | Structure | %RF | Rescue Coefficient | FRF |
|---|---|---|---|---|
| agmatine | 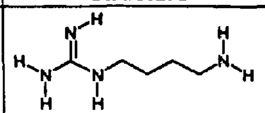 | 29 | 1.7 | 17 |
| A | 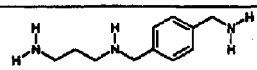 | 100 | 0.83 | 120 |
| B | 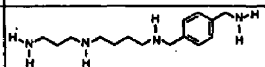 | 91 | 1.1 | 83 |
| C | 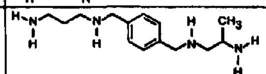 | 65 | 1.5 | 43 |
| D | 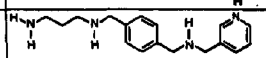 | 64 | 1.5 | 43 |
| E | 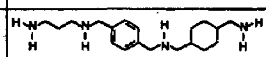 | 96 | 1.2 | 80 |
| F | 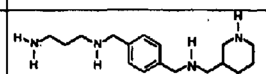 | 116 | 1.23 | 94 |
| G | 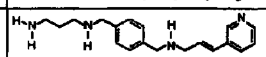 | 105 | 1.14 | 92 |
| H | 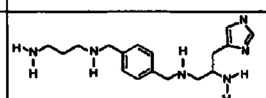 | 150 | 1.53 | 98 |
| I | 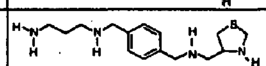 | 132 | 1.29 | 102 |
| J | 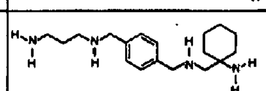 | 108 | 0.99 | 109 |
| K | 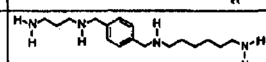 | 123 | 0.81 | 152 |
| L | 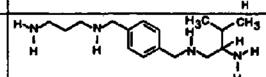 | 92 | 0.5 | 184 |
| M | 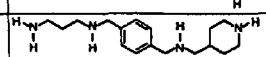 | 176 | 1.3 | 135 |
| N | 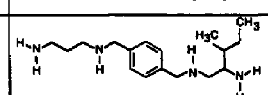 | 102 | 0 | — |
| O | 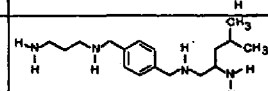 | 71 | 0 | — |
| P | 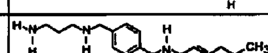 | 77 | 0 | — |
| Q | 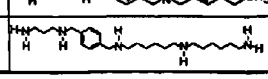 | 146 | 0.41 | 356 |

FIG. 1

| ID | Structure | %RF | Rescue Coefficient | FRF |
|---|---|---|---|---|
| R | 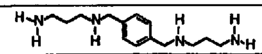 | 141 | 0.17 | 829 |
| S | 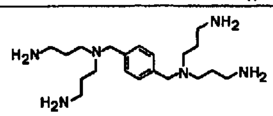 | 100 | 0.54 | 185 |
| T | 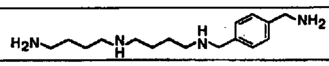 | 129 | 1.28 | 101.2 |
| U | 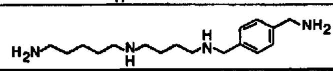 | 143 | 1.3 | 109.8 |

POLYAMINE ANALOGS THAT ACTIVATE ANTIZYME FRAMESHIFTING

CROSS-REFERENCE TO RELATED APPLICATIONS

This application is a continuation-in-part of U.S. patent application Ser. No. 10/251,819, filed Sep. 23, 2002 now U.S. Pat. No. 6,914,079.

STATEMENT REGARDING FEDERALLY SPONSORED RESEARCH OR DEVELOPMENT

Not applicable

REFERENCE TO A COMPACT DISK APPENDIX

Not applicable

TECHNICAL FIELD

The present invention relates to novel polyamines, their synthesis and use in pharmacological, cosmetic or agricultural applications. The instant invention provides polyamines that induce antizyme production which in turn down regulates both the production of polyamines by ornithine decarboxylase (ODC) and the transport of polyamines by its corresponding polyamine transporter. These compounds will preferably enter the cell independent of the polyamine transporter. As drugs, these compounds are used to treat any disease associated with cellular proliferation including but not limited to cancer. As such, they will be useful as drugs to treat diseases where components of the immune system undergo undesired proliferation. These compounds will also be effective for the treatment of unwanted proliferation of hair on skin. The present invention also identifies key structural elements expected to comprise the antizyme inducing motif(s) of small molecules related to polyamines.

BACKGROUND OF THE INVENTION

The endogenous polyamines, putrescine, spermidine, and spermine contribute to many essential cellular functions through their interactions with DNA, RNA, proteins, and lipids (Pegg, A. E. *Cancer Res.* 48:759–774 (1988); Heby, O. et. al., *Trends Biochem. Sci.* 15:153–158 (1990); Jänne, J. et. al., *Ann. Med.* 23:241–259 (1991); Brooks, W. H. *Med Hypotheses* 44:331–338 (1995); Igarashi, K. et. al., *Biochem. Biophys. Res. Commun.* 271:559–564 (2000); Casero, R. A. et. al., *J. Med. Chem.* 44:1–26 (2001)). Polyamines are essential for cell proliferation through their involvement in DNA replication, cell cycle regulation, and protein synthesis. Depletion of intracellular polyamine levels inhibits cell growth. Antizyme regulates polyamine levels both by inhibiting polyamine biosynthesis and uptake/import. The importance of their function is highlighted by the fact that specific biosynthesis, degradation, uptake and excretion pathways tightly control cellular polyamine levels (Heby, O. *Differentiation* 19:1–20 (1981); Seiler, N. et. al., *Int. J. Biochem.* 22:211–218 (1990); Seiler, N. et. al., *J. P. Int. J. Biochem. Cell Biol.* 28:843–861 (1996)). Excessive cell growth has been correlated with high levels of intracellular polyamines (Pegg, A. E. *Cancer Res.* 48:759–774 (1988)). Numerous tumor cell types have been analyzed and shown to have higher polyamine levels than normal, non-tumorigenic cells. Within a single tumor type, the more highly malignant tumors often have higher polyamine levels (Kurihara, H. et. al., *Neurosurgery* 32:372–375 (1993)). For these reasons, depletion of intracellular polyamine levels is an attractive approach for the inhibition of uncontrolled or undesirable cell growth.

Ornithine decarboxylase (ODC) is the rate-limiting enzyme of cellular polyamine synthesis, converting omithine to putrescine. Putrescine is then converted to both spermidine and spermine by the sequential transfer of an aminopropyl group from decarboxylated —S-adenosylmethionine. Increasing concentrations of intracellular polyamine levels induce the production of antizyme which negatively regulates ODC by binding to it and targeting it for destruction. Antizyme has also been shown to inhibit polyamine uptake (Mitchell, J. L. et. al., *Biochem. J.* 299: 19–22 (1994); Suzuki, T. et. al., *Proc. Natl. Acad. Sci. USA* 91: 8930–8934 (1994); Sakata, K. et. al., *Biochem. Biophys. Res. Commun* 238:415–419 (1997)) and recent evidence suggests that antizyme may increase polyamine excretion (Sakata, K. et. al., *Biochem J.* 347:297–303 (2000)). Therefore, antizyme can very effectively limit the accumulation of cellular polyamines.

Antizyme has been found in vertebrates, fungi, nematodes, insects and eukaryotes (Ivanov, I. et. al., *Nucleic Acids Res.* 28:3185–3196 (2000)). Three antizyme isoforms, AZ1, AZ2 and AZ3, have now been identified among vertebrates. Both AZ1 and AZ2 have wide tissue distribution but AZ2 mRNA is less abundantly expressed. AZ3 is expressed only in the testis germ cells (Ivanov, I. et. al., *Proc. Natl. Acad. Sci. USA* 97: 4808–4813 (2000); Tosaka, Y. et. al., *Genes to Cells* 5:265–276 (2000)) where expression begins early in spermiogenesis and finishes in the late spermatid phase. Antizyme production is controlled by a unique regulatory mechanism known as translational frameshifting (Matsufuji, S. et. al., *Cell* 80: 51–60 (1995)). The antizyme gene consists of two overlapping open reading frames (ORFs). The bulk of the coding sequence is encompassed in the second (ORF2) but it does not contain an initiation codon. ORF1 is short but contains two AUG initiation codons. Either one of the initiation codons can be used to initiate translation but normally little full length mRNA is made unless a +1 frameshift occurs just before the ORF1 UGA stop codon enabling translation to continue. Only minute quantities of antizyme are generally present in mammalian tissues. Polyamines and agniatine have been found to greatly enhance the efficiency of frameshifting (Hayashi, S. et. al., *Trends Biochem. Sci.* 21:27–30 (1996); Satriano, J. et. al., *J. Biol. Chem.* 273:15313–15316 (1998)). Vertebrates possess three elements that control frameshifting, the UGA stop codon in ORF1, a stem-loop structure 3' to the ORF1 UGA that can base pair with a portion of the loop and conserved sequence motifs within the 3' region of ORF1 (Matsufuji, S. et. al., *Cell* 80: 51–60 (1995)). It is unclear how or if polyamines interact directly with these structural elements to induce frameshifting. It is possible that there are unknown mediators that may involve the ribosome.

ODC is enzymatically active only as a homodimer since the active site contains structural contributions from both monomers. The interaction between the monomers is weak; whereas, antizyme has a high affinity for the ODC monomer. Antizyme binding disrupts the homodimer interface leading to the formation of two antizyme-ODC heterodimers that are now enzymatically inactive (Kameji, T. et. al., *Biochim. Biophys. Acta* 717:111–117 (1982); Kern, A. D. et. al., *Struct. Fold. Des.* 7:567–581 (1999)). Antizyme directs the ODC monomer to the proteosome where it is degraded without ubiquitination (Murakami, Y. et. al., *Nature* 360:

597–599 (1992); Tokunaga, F. et. al., *J. Biol. Chem.* 269: 17382–17385 (1994)). Antizyme is then released and free to interact with and destroy additional ODC monomers in a catalytic fashion. The AZ2 isoform has not been shown to catalytically induce the degradation of ODC, although AZ2 has been shown to inhibit both ODC and polyamine uptake equipotently (Zhu, C. et. al., *J. Biol. Chem.* 274:26425–26430 (1999). AZ3 is the most recently discovered antizyme and has also been shown to inhibit ODC (Ivanov, I. et. al., *Proc. Natl. Acad. Sci. USA* 97:4808–4813 (2000); Tosaka, Y. et. al., *Genes to Cells* 5:265–276 (2000)).

Antizyme is regulated by antizyme inhibitor, which has a higher affinity towards antizyme than ODC (Fujita, K. et. al., *J. Biol. Chem.* 274:26424–26430 (1982); Kitani, T. et. al., *Biochim. Biophys. Acta* 991:44–49 (1989); Murakami, Y. et. al., *Biochem. J.* 259:839–845 (1989)). Thus it may rescue ODC from degradation by displacing it from antizyme. Antizyme inhibitor, like ODC, forms a homodimer and has a high degree of sequence homology with ODC. However, it does not form heterodimers with ODC (Murakami, Y. et. al. *J. Biol. Chem.* 271:3340–3342 (1996)) and lacks ODC activity. Antizyme inhibitor has been shown to be rapidly induced in growth-stimulated fibroblasts and release ODC from antizyme suppression (Nilsson, J. et. al., *Biochem. J.* 346:699–704 (2000)).

Frameshifting can be detected using a dual luciferase reporter system that measures the efficiency of antizyme translational frameshifting (Grentzmann, G. et. al., *RNA* 4:479–486 (1998); Howard, M. et. al., *Genes to Cells* 6:931–941 (2001)). Frameshifting efficiency is determined by comparing the ratio of firefly luciferase to renilla luciferase activity in cells transfected in parallel using a control vector containing a constitutive +1 frameshift (AZ-IF) that measures the in-frame translation efficiency and a vector containing the inducible 0 to +1 frameshift (AZ1) construct. In these constructs, the renilla luciferase gene is upstream of the firefly luciferase gene which are separated by a short cloning sequence containing the portions of antizyme 1 and 2 known to contain the mRNA signals for polyamine stimulated frameshifting. Using a 96-well format, this assay system gives a quantitative measure of the efficiency of the polyamines, polyamine analogs and other compounds to induce frameshifting in a cell-based bioassay. Cells must be pretreated with α-difluoromethylornithine (DFMO), an irreversible inhibitor of ODC, prior to screening to decrease the basal antizyme frameshifting levels and increase the sensitivity to polyamine or compound-mediated stimulation of antizyme frameshifting.

In one of the first systematic assessments of antizyme induction by polyamine analogs, oligoamines such as octamines, decamines and dodecamines were found to induce antizyme to varying degrees (Mitchell, J. L. A. et. al., *Biochem. J.* Vol. 366, p. 663–671, 2002). These levels correlated with the cellular levels of antizyme as measured by Western blotting. The differences in the levels of antizyme appeared to be a result of dissimilar rates of protein synthesis since the half-life of antizyme (T½~75 min.) did not appear to be controlled by the polyamine analog. Therefore, it is presumable that the analogs have varying abilities to stimulate the +1 translational frameshift. A number of compounds such as bisethylnorspermine, bisethylhomospermine and 1,19-bis(ethylamino)-5,10,15-triazanonadecane (BE-4-4-4-4) were found to induce antizyme as well as spermine. However, certain conformational restrictions within the polyamine analogs such as three, four and five-membered rings or triple bonds between the central nitrogens negatively affected antizyme induction. Many of the oligoamines greatly exceeded spermine in their ability to induce antizyme (super-induction) when tested at the same concentration (10 µM). The amount of antizyme frameshifting was found to correlate with the degree of growth inhibition. The oligoamines induced immediate cessation of cell growth, which was speculated to result from the super-induction of frameshifting. However, the authors also noted that these compounds might have other mechanisms of action leading to their observed cytotoxicity.

It is plausible that some antizyme inducers will also directly inhibit the enzymatic activity of ODC. A number of putrescine analogs have been found to be potent reversible inhibitors of ODC. For example, 1,4-diamino-trans-2-butene inhibits ODC with a $K_i$ of 2 µM and 1,4-phenylene-diamine somewhat less potently inhibits ODC with a $K_i$ of 46 µM (Relyea, N. et. al., *Biochem. Biophys. Res. Comm.* 67:392–402 (1975); Solano, F. et. al., *Int. J. Biochem.* 20:463–470 (1988). Compounds of this nature may enhance polyamine depletion because ODC is inhibited in both a direct and indirect manner through induction of antizyme.

Polyamines may arrest prostate cell growth in the G1 phase by inducing antizyme. The prostate is the only vertebrate organ that synthesizes polyamines for export. As such, this tissue is exposed to higher concentrations of the polyamines. Spermine has been found to be a naturally occurring inhibitor of prostatic carcinoma cell growth in vitro and in vivo (Smith, R. C. et. al., *Nature Med.* 1:1040–1045 (1995)). Subsequently, it was found that spermine could induce G1 arrest in poorly metastatic prostatic carcinomas but not in highly malignant cells (Koike, C et. al., *Cancer Res.* 59:6109–6112, (1999)). Furthermore, antizyme could be induced only in the poorly metastatic prostatic carcinomas. Antizyme was later found to affect the cell-cycle of prostatic carcinoma cells with the discovery that it could interact with G1 cyclin D1 and its associated cyclin-dependent kinase, cdk4 (Coffino, P. *Nat. Rev. Mol. Cell. Biol.* 2:188–194 (2001)). The degradation of cdk4 and cyclin D1 were dependent on antizyme and independent of ubiquitin using in vitro purified proteasomes. The steady-state levels of the cyclin and kinase decreased when the polyamine levels were experimentally raised in the cultured cells. It has been proposed that prostatic cells that lose the ability to activate antizyme may eventually become malignant (Koike, C et. al., *Cancer Res.* 59:6109–6112, (1999)).

A number of studies have looked at both transient and inducible overexpression of antizyme in cell lines and animal models. Anti-tumor activity was shown in a study by Iwata and colleagues (Iwata, S. et. al., *Oncogene* 18:165–172 (1999)) using ectopically expressed inducible antizyme. In this study, nude mice were inoculated with H-ras transformed NIH3T3 cells expressing an inducible antizyme vector. Induction of antizyme blocked tumor formation in these mice and induced cell death in vitro. Intracellular polyamine levels were also measured. Both putrescine and spermine were completely depleted within 12 hours of induction. Spermine was also significantly reduced but over a slower time frame. Some of these observations were verified in another report that used a glucocorticoid (dexamethasone)—inducible promoter to force expression of antizyme in HZ7 cells (Murakami, Y. et. al., *Biochem. J.* 304:183–187 (1994)). Dexamethasone inhibited growth of this cell line, depleted putrescine levels, severely decreased spermidine levels but did not affect spermine levels. Addition of exogenous putrescine restored the intracellular putrescine levels and partially restored spermidine levels. In a third study, Tsuji and colleagues (Tsuji, T. et. al., *Oncogene* 20:24–33 (2001)) developed a hamster malignant oral keratinocyte (HCPC-1) cell line that stably expressed antizyme. Ectopic expression of antizyme suppressed tumor mass in nude mice by about 50%. In vitro, ectopic expression significantly increased the doubling time of antizyme transfectants and the antizyme transfectants demonstrated significantly less growth in soft agar. There was also a substantial increase in G1 phase cells with a corresponding decrease in S phase cells. These cells also showed morphological alterations suggesting terminal differentiation. This was accompanied by an increase in demethylation of DNA CCGG sites of 5-methyl cytosines. It was proposed that antizyme mediates a novel mechanism in tumor suppression by reactivating key cellular genes silenced by DNA hypermethylation during cancer development. In yet another example, transgenic mice that overexpress ODC in keratinocytes have been shown to develop a high rate of spontaneous and induced skin cancer (Megosh, L. et. al., *Cancer Res.* 55:4205–4209 (1995)). A reduction in the frequency of induced skin-tumors was observed in the skin of these transgenic mice expressing antizyme (Feith, D. et. al. *Cancer Res.* 61:6073–6081 (2001)).

Polyamines have been found to play a central role in hair follicle cell growth, a highly proliferative tissue, with a cell turnover time of between 18–23 hours. ODC plays a functional role in hair follicle growth, which is characterized by cyclic transformations from active growth and hair fiber production (anagen) through regression (catagen) into a resting phase (telogen). In mice, ODC is expressed in ectodermal cells at sites where hair follicles develop during embryonic development (Nancarrow, M. J., et. al., *Mech. Dev.* 84: 161–164 (1999); Schweizer, J. In: *Molecular Biology of the Skin: The Keratinocyte*, Darmon M, et. al., Eds., Academic Press, New York, 1993, pp 33–78). In proliferating bulb cells of anagen follicles, ODC is abundantly expressed except for a pocket of cells at its base. ODC protein expression is down regulated when the hair follicle enters catagen and is not detected in telogen. ODC protein expression does not resume until new follicle formation commences. A more complex expression of ODC is found in vibrissae (beard hair). ODC is expressed in the keratinocytes of the vibrissal hair shaft as well as in the bulb and outer root sheath cells near the follicle bulge. In comparison, ODC expression is very low in interfollicular epidermis.

Numerous studies have shown that inhibition of ODC with DMFO, an irreversible inhibitor of ODC, reduces hair growth in mammals. Mice were found to have reduced hair growth when DFMO was systemically delivered via the drinking water (Takigawa, M. et. al., *Cancer Res.* 43:3732–3738 (1983)). Intravenous administration of DFMO decreased wool growth in sheep (Hynd, P. I. et. al., *J. Invest. Dermatol.* 106:249–253 (1996)) and oral administration of DFMO in cats and dogs produced alopecia and dermatitis (Crowell, J. A. et. al., *Fundam. Appl. Toxicol.* 22:341–354 (1994)). Additional evidence that ODC plays a role in hair follicle regulation resulted from a study in humans that were being treated for acute *Trypanosoma brucei* infections (African sleeping sickness) (Pepin, J. et. al. *Lancet* 2:1431–1433 (1987)) using DFMO. Patients using this treatment showed signs of hair loss mainly on the scalp but it was reversible after discontinuing treatment.

The development of a number of transgenic mice either overexpressing spermidine/spermine N1-acetytransferase (SSAT) or ODC have contributed additional evidence that distorted tissue polyamine pools leads to hair loss (Pietila, M. et. al., *J. Biol. Chem.* 272:18746–18751 (1997); Suppola, S. et. al., *Biochemistry* 7338:311–316 (1999); Megosh, L. et. al., *Cancer Res.* 55:4205–4209 (1995)). SSAT is a key enzyme in the catabolism of polyamines that is rate-limiting for the conversion of spermine to spermidine and spermidine to putrescine. Both transgenic animal models showed permanent hair loss in which the normal hair follicles were transformed into dermal cysts that progressively increased in size as the animals aged (Pietilä, M. et. al., *J. Biol. Chem.* 272:18746–18751 (1997); Suppola, S. et. al., *Biochemistry* 7338:311–316 (1999); Soler, A. P. et. al., *J. Invest. Dermatol.* 106, 1108–1113 (1996); Megosh, L. et. al., *Cancer Res.* 55:4205–4209 (1995)). This was manifest as a thickening and excessive skin folding of the epidermis. The common phenotypic feature that each of these animal models shared was a massive over accumulation of putrescine in the skin (Pietila, M. et. al., *J. Invest. Dermatol.* 116:801–805 (2001)). It was proposed that elevated levels of polyamines and especially putrescine favor continuous proliferation of epithelial cells leading to the formation of follicular cysts and hair loss. Low levels of putrescine favor differentiation of the outer root sheath keratinocytes and are not permissive for proliferation.

Polyamine biosynthesis has also been shown to be essential during the activation of immunocompetent cells (Fillingame, R. H. et. al., *Proc. Natl. Acad. Sci. USA* 72:4042–4045, (1975); Korpela, H. et. al., *Biochem. J.* 196:733–738 (1981)). Studies with DFMO confirm that polyamine depletion therapy can inhibit the immune response and may be a successful therapy against a number of autoimmune diseases. Both humoral and cell-mediated immune responses were affected by the anti-proliferative effect of polyamine depletion. DFMO treatment of mice challenged with tumor allografts resulted in modified cytotoxic T-lymphocyte and antibody responses (Ehrke, J. M. et. al., *Cancer Res.* 46:2798–2803 (1986)). Reports by Singh et al. indicate that DFMO treatment may also ameliorate acute lethal graft versus host (ALGVH) disease in mice (Singh, A. B. et. al., *Clin. Immunol. Immunopathol.* 65:242–246 (1992)). Murine ALGVH represents a model of human GVH that contributes to the morbidity and mortality of bone marrow transplantation in humans and is characterized by anemia and the loss of T cell function and numbers. In this study, treatment of ALGVH mice with DFMO decreased mortality and anemia while preserving the cytotoxic T cell and natural killer cell population of the host. Polyamine depletion therapy using DFMO has also been shown to benefit lupus-prone female NZB/W mice (Thomas, T. J. et. al., *J. Rheumatol.* 18:215–222 (1991)). Anti-DNA antibody production, immunoglobulin G and A synthesis, proteinuria and blood urea nitrogen were significantly reduced in treated mice.

Chemotherapeutics and radiation therapies target rapidly dividing cancer cells but they inadvertently affect the rapidly dividing epithelial cells of the mouth and intestine, hair follicles and hematopoietic cells in bone marrow. If the epithelial cells of the mouth or intestine become damaged and depleted, thinning and ulceration can result (mucositis) leading to pain and potential infection. Oral mucositis is also the result of damaged stem cells. Oral tissues are particularly painful if damaged.

Under normal conditions, the lining of the intestine is continuously being renewed through the proliferation of epithelial stem cells and their progeny in the crypts of villi (Booth, D, et. al., *J Natl Cancer Inst Monogr* 29:16–20 (2001)). When damage occurs (e.g., radiation or cytotoxic insult), a burst of proliferation/regeneration occurs in undamaged stem cells. A number of proposals to limit the damage to stem cells and enhance regeneration have been made. One strategy has been to arrest the cell cycle progression and accumulate cells in $G_0$ or $G_1$ during radiation or chemotherapy treatment to make them more resistant to damage. Other strategies include increasing the number of stem cells prior to potential damage or enhancing proliferation after damage (Farrell, C. L. et. al., *Cancer Res.* 58: 933–939 (1998)). Polyamines are taken up from the gut by normal and neoplastic epithelial cells of the gut mucosa, especially during periods of cell proliferation (Milovic V. et. al., *Eur J Gastroenterol Hepatol.* 13:1021–5 (2001)). The involvement of polyamines in proliferation of intestinal epithelial cells has been demonstrated using the nontransformed small intestinal cell line from rats, IEC-6, where polyamines increased DNA synthesis (Olaya, J. et. al. *In Vitro Cell Dev Biol. Anim.* 35:43–8, (1999)). The chemotherapeutic agent camptothecin, a DNA topoisomerase I inhibitor, can induce apoptosis in IEC-6 cells. However, reducing polyamines can have a protective effect. When IEC-6 cellular polyamines were reduced with DFMO, apoptosis due to camptothecin was delayed (Ray, R. M. et. al., *Am J Physiol Cell Physiol* 278:C480–489 (2000)). This may be due to $G_1$ cell cycle arrest, which has been demonstrated to occur in IEC-6 cells incubated with DFMO (Ray R. M. et. al. *Am. J. Physiol.* 276:C684–91 (1999)). A more efficient depletion of polyamines with synthesis and uptake inhibition through induction of antizyme could provide significant protection against mucositis after radiation or chemotherapy.

BRIEF SUMMARY OF THE INVENTION

Ideal polyamine analogs should not substitute for the normal physiological functions of polyamines such as having the ability to rescue cells from DFMO-induced growth inhibition in vitro. It is also desirable that these compounds not be readily metabolized to regenerate polyamines. Identifying compounds that induce frameshifting and ultimately increase full length antizyme protein levels will be useful for depleting intracellular polyamine levels. These compounds should be an effective therapy for any disease associated with cellular proliferation including but not limited to cancer. As such, they are useful as drugs in a number of diseases where components of the immune system undergo undesired proliferation. Non-limiting examples include asthma, inflammation, autoimmune diseases, psoriasis, restenosis, rheumatoid arthritis, scleroderma, systemic and cutaneous lupus erythematosus, Type I insulin dependent diabetes, tissue transplantation, osteoporosis, hyperparathyroidism, treatment of peptic ulcer, glaucoma, Alzheimer's disease, Crohn's disease and other inflammatory bowel diseases. Other disease states associated with the proliferation of fungal, bacterial, viral and parasitic agents such as African sleeping sickness are also included. These compounds will also be effective for the treatment of unwanted proliferation of hair on skin. Antizyme inducers will be useful in the treatment of diseases involving the cell cycle by pausing the cell cycle progression during radiation or chemotherapy treatment. The appropriate cells will accumulate in $G_0$ or $G_1$, protecting them from radiation or chemotherapy induced hair loss (alopecia) and mucositis.

BEST AND VARIOUS MODES FOR CARRYING OUT INVENTION

Figure 1:
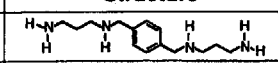
FIG. 1 is a tabular representation of a large number of polyamine analogs A-S (25 μM) that were tested for their ability to induce antizyme frameshifting using the dual luciferase reporter assay.
Figure 1:
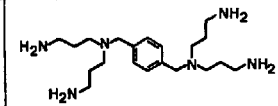
Figure 1:
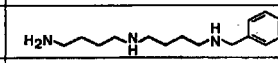
Figure 1:
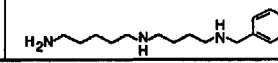

The analogs and derivatives that can be used according to the present disclosure include those encompassed by the following formula I:

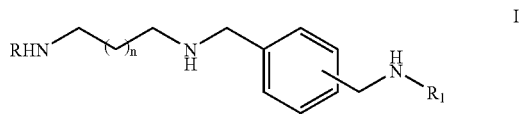

wherein, n can be 0 to 8 and the aminomethyl functionality can be ortho, meta or para substituted, R is hydrogen, —$CH_3$, —$CH_2CH_3$, 2-aminoethyl, 3-aminopropyl, 4-aminobutyl, 5-aminopentyl, 6-aminohexyl, 7-aminoheptyl, 8-aminooctyl, N-methyl-2-aminoethyl, N-methyl-3-aminopropyl, N-methyl-4-aminobutyl, N-methyl-5-aminopentanyl, N-methyl-6-aminohexyl, N-methyl-7-aminoheptyl, N-methyl-8-aminooctyl, N-ethyl-2-aminoethyl, N-ethyl-3-aminopropyl, N-ethyl-4-aminobutyl, N-ethyl-5-aminopentyl, N-ethyl-6-aminohexyl, N-ethyl-7-aminoheptyl or N-ethyl-8-aminooctyl and $R_1$ is a moiety selected from the group consisting of a hydrogen or a straight or branched C1–20 saturated or unsaturated aliphatic; aliphatic amine but not propylamine when R=H, n=1 and the aminomethyl functionality is para substituted; an alicyclic; single or multi-ring aromatic; single or multi-ring aryl substituted aliphatic; aliphatic-substituted single or multi-ring aromatic; a single or multi-ring heterocyclic, a single or multi-ring heterocyclic-substituted aliphatic; an aliphatic-substituted aromatic; and halogenated forms thereof.

The compounds induce expression of full-length antizyme without replacing the functionality of the native polyamines.

In preferred embodiments of the invention, the analogs and derivatives that can be used according to this disclosure can be further modified as described in formula II:

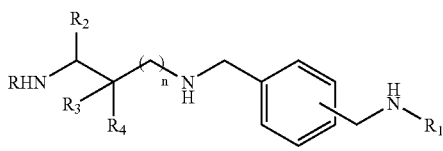

II wherein n can be 0 to 8, R and $R_1$ are described as above, $R_2$ can be independently selected from hydrogen, —$CH_3$ or —$CH_2CH_3$ and $R_3$ and $R_4$ may be the same or different and are independently selected from hydrogen, or flourine.

An additional preferred embodiment of compounds that can be used according to this disclosure are described in formula III:

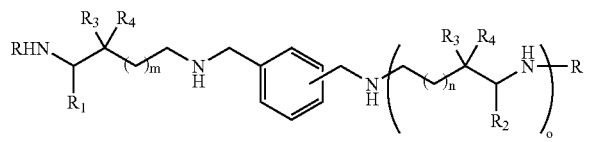

III wherein, m and n can be 0 to 7 independently, but m cannot equal n when $R_1$ equals $R_2$ and $R_3$ equals $R_4$, R can be 2 to 4, R can be independently selected from H, —$CH_3$ or —$CH_2CH_3$, $R_1$ and $R_2$ can be independently selected from hydrogen, —$CH_3$ or —$CH_2CH_3$ and $R_3$ and $R_4$ may be the same or different and are independently selected from hydrogen or fluorine.

Another aspect of the present invention are compounds of formula IV:

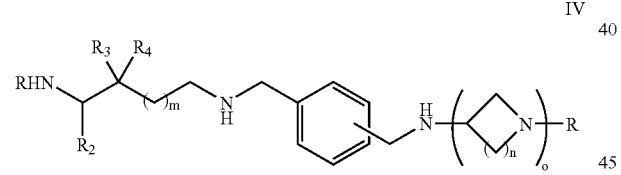

IV wherein, R is hydrogen, —$CH_3$, or —$CH_2CH_3$, m and n can be 0 to 7 independently and o can be 2 to 4, $R_2$ can be independently selected from hydrogen, —$CH_3$ or —$CH_2CH_3$ and $R_3$ and $R_4$ may be the same or different and are independently selected from hydrogen or fluorine.

In a further aspect of the invention, compounds of the present invention are represented by formula V

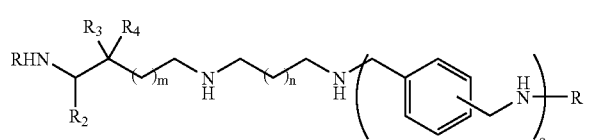

V wherein, R is hydrogen, —$CH_3$, or —$CH_2CH_3$, m can be 0 to 7, n can be 0 to 8 and o can be 2 to 4, $R_2$ can be independently selected from hydrogen, —$CH_3$ or —$CH_2CH_3$ and $R_3$ and $R_4$ may be the same or different and are independently selected from hydrogen or fluorine.

The present disclosure also relates to novel compounds of formulae I, II, III, IV and V above with the further proviso that the novel compounds are non-symmetrical substituted xylene derivatives.

In other words, in formula I,

differs from

In formula II,

differs from

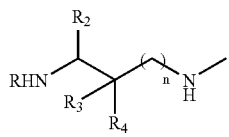

and in formula III

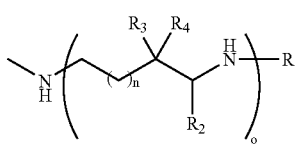

differs from

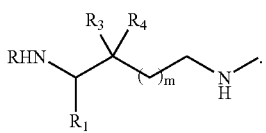

Preferred novel compounds according to the present disclosure are those compounds wherein only one side of the xylene ring contains a group other than with the most preferred compounds being B, T and U as shown in FIG. 1.

As drugs, the polyamine analogs decrease cellular polyamine levels and can be used to treat disorders of undesired cell proliferation, including cancer, viral infections and bacterial infections. The invention additionally encompasses the stabilization of polyamine analogs by modifying them to resist enzymatic degradation. Such modifications include substitution of primary amine groups with alkyl groups, the addition of alkyl groups to the terminal amino groups and the addition of fluorine atoms μ to the terminal amino groups.

Additionally, it is desirable that the polyamine analogs of the invention enter cells by pathways other than those of active polyamine transport regulated by antizyme. Thus, an additional embodiment of the invention are analogs that are not imported into cells primarily by the polyamine transporters. Frameshifting activity is only one of the requirements for a good antizyme inducer. According to the present invention, it is preferable that the compounds enter the cell independent of the polyamine transporter since antizyme expression is known to inhibit polyamine transport. It has been determined by the present inventors that ideal candidates should not substitute for the normal physiological functions of polyamines such as having the ability to rescue cells from DFMO induced growth inhibition in vitro. Moreover, according to the present invention, it is also desirable that these compounds not be readily metabolized to regenerate polyamines. It is believed, pursuant to this invention, that any compound with frameshifting activity that could substitute for or degrade to a polyamine would be expected to defeat the goal of decreasing polyamine levels. Compounds, as determined by the present inventors, should be selective for antizyme frameshifting activity, exhibiting little affinity for the biosynthetic or catabolic enzymes associated with polyamine regulation such as ODC or SSAT. Compounds that fit into the above categories should deplete intracellular polyamine levels at concentrations known to induce frameshifting.

The present invention also relates to pharmaceutical compositions comprising an effective amount of at least one of the above disclosed compounds.

A further aspect of the present invention relates to treating a condition associated with cellular proliferation by administering at least one of the compounds described above.

The present disclosure also relates to treating one or more conditions associated with cellular proliferation comprising administration of at least one of B, T or U shown in FIG. 1. These conditions include, but are not limited to condition is selected from the group consisting of cancer, mucositis, asthma, inflammation, autoimmune disease, psoriasis, restentosis, rheumatoid arthritis, scleroderma, systemic and cutaneous lupus erythematosus, Type I insulin dependent diabetes, tissue transplantation, osteoporosis, hyperparathyroidism, treatment of peptic ulcer, glaucoma, Alzheimer's disease, and inflammatory bowel diseases.

The administration can be systemic, for example, and can be oral. In addition, the administration can be via a time-release vehicle, if desired. Also, if desired, the compounds R and S can be formulated as a cosmetic.

Another aspect of the present invention relates to inhibiting hair growth comprising topical administration of at least one of B, T or U shown in FIG. 1 to a subject in need of hair growth inhibition.

The present invention also relates to of inhibiting hair loss (alopecia) comprising topical administration of at least one of B, T or U shown in Figure to a subject undergoing radiation or chemotherapy.

Compounds B, T and U can also be used to treat conditions from fungal, bacterial, viral and parasitic agents.

Listed below are definitions of various terms used to describe this invention. These definitions apply to the terms as they are used throughout this specification, unless otherwise limited in specific instances, either individually or as part of a larger group.

The term "aryl" refers to monocyclic or bicyclic aromatic hydrocarbon groups having 6 to 12 carbon atoms in the ring portion, such as phenyl, naphthyl, biphenyl and diphenyl and diphenyl groups, each of which may be substituted.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms.

Examples of suitable alkyl groups include methyl, ethyl and propyl. Examples of branched alkyl groups include isopropyl and t-butyl.

The term "halogen" or "halo" refers to fluorine, chlorine, bromine and iodine.

The alkoxy groups typically contains about 1–8 carbon atoms and more typically about 1–4 carbon atoms. Examples of suitable alkoxy groups are methoxy, ethoxy and propoxy.

Examples of some suitable alkaryl groups include phenyl $C_{1-3}$ alkyl such as benzyl.

Examples of some substitution groups are $NO_2$, alkyl, $CF_3$, alkoxy and halo.

Examples of suitable cycloalkyl groups typically contain 3–8 carbon atoms and include cyclopropyl, cyclobutyl, cyclopentyl and cyclohexyl.

Examples of fused bicyclic unsatured ring groups are 2-quinolinyl, 3-quinolinyl, 5-quinolinyl, 6-quinolinyl, 7-quinolinyl, 1-isoquinolinyl, 3-isoquinolinyl, 6-isoquinolinyl, 7-isoquinolinyl, 3-cinnolyl, 6-cinnolyl, 7-cinnolyl, 2-quinazolinyl, 4-quinazolinyl, 6-quinazolinyl, 7-quinazolinyl, 2-quinoxalinyl, 5-quinoxalinyl, 6-quinoxalinyl, 1-phthalaonyl, 6-phthalazinyl, 1–5-naphthyridin-2-yl, 1,5-naphthyridin-3-yl, 1,6-naphthyridin-3-yl, 1,6-naphthyridin-7-yl, 1,7-naphthyridin-3-yl, 1,7-naphth7yridin-6-yl, 1,8-naphthyrdiin-3-yl, 2,6-naphthyridin-6-yl, 2,7-naphthyridin-3-yl, indolyl, 1H-indazolyl, purinyl and pteridinyl. Substitutions for each of the fused ring groups include the above noted group of substituents described herein.

Examples of mono- and multi-ring groups include aryl and bicyclic fused aryl-cycloalkyl groups. The aryl groups include an aromatic substituent which can be a single ring of multiple rings (up to three rings) which are fused together or linked covalently. The rings may each contain from zero to four heteroatoms selected from N, O and S, wherein the nitrogen and sulfur atoms are optionally oxidized, and the nitrogen atom(s) are optionally quartemized. Non-limiting examples of aryl groups include phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-uinoxalinyl, 3-quinolyl and 6-quinolyl. Substitutions for each of the above noted aryl systems include the above noted group of substitutents described herein.

The "bicyclic fused aryl-cycloalkyl" groups are those groups in which an aryl ring (or rings) is fused to a cycloalkyl group (including cyclohetreroalkyl groups. The group can be attached to the remainder of the molecule through either an available valence on the aryl portion of the group, or an available valence on the cycloalkyl portion of the group. Examples of such benzotetrahydropyranyl and 1,2,3,4-tetrahydronaphthyl. Substitutents for each of the above noted groups include the group of substituents described herein.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The present invention includes the free base or acid forms, as well as salts thereof, of the polyamines and derivatives described by the above formulas. The invention also includes the optical isomers of the above described analogs and derivatives. In a further embodiment of the invention, mixtures of enantiomers and/or diastereoisomers, resulting from a single preparative step, combination, or interconversion are encompassed.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynl, cycloalkyl or cycloalkenyl groups as defined beginning on Page 7.
(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCRO$_2$R) or —NHCR(=CHCRONR$_2$)
(e) Schiff Bases, —N=CR$_2$
(f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p.30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels. Another prodrug derived from a carboxylic acid form of the invention may be a quaternary salt type

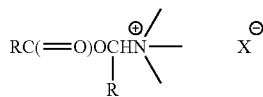

of structure described by Bodor et al., J. Med. Chem. 1980, 23, 469.

It is of course understood that the compounds of the present invention relate to all optical isomers and stereoisomers at the various possible atoms of the molecule.

The compounds used in the methods of this invention form pharmaceutically acceptable acid and base addition salts with a wide variety of organic and inorganic acids and bases and includes the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamnate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide potassium hydroxide, ammonium hydroxide, potassium carbonate, methylamine, diethylamine, and ethylene diamine.

The invention also provides prodrug forms of the above described compounds and derivatives, wherein the prodrug is metabolized in vivo to produce a compound or derivative as set forth above. Indeed, some of the above described compounds or derivatives may be a prodrug for another compound or derivative. This scenario is plausible if the prodrug is a substrate for either spermidine synthase or spermine synthase which are enzymes that transfer an aminopropyl group to putrescine and spermidine, respectively.

The compounds may be utilized alone or in combination with other agents, particularly other inhibitors of polyamine synthesis or transport, but including other inhibitors of cell proliferation. Without being bound by theory, the polyamines compound of the invention may decrease polyamine levels by inducing antizyme (AZ), which in turn down regulates both the production of polyamines by omithine decarboxylase (ODC) and the transport of polyamines by its corresponding transporter. Polyamine levels may also decrease because antizyme may induce increases in polyamine excretion. The invention further defines structural elements/motifs within these compounds that appear key to their induction of antizyme as determined by assays. Because polyamines are absolutely essential for DNA replication and are essential to cellular homeostasis, there is an interest in preventing cell proliferation by lowering intracellular polyamine levels. Sufficiently low polyamine levels can lead to cell death. Thus any agent able to lower polyamine levels, particularly by inhibiting both polyamine biosynthesis and uptake/import, offers the opportunity to target a variety of disease or undesirable conditions related to cell proliferation, including cancer.

The compounds of the invention are not necessarily metabolized like naturally occurring polyamines. As such, the compounds of the invention may have the advantage of not being readily metabolized to regenerate polyamines. Administration of polyamine compounds, which are subject to conversion to putrescine and other polyamines, would be expected to defeat the goal of decreasing polyamine levels. Thus one aspect of the invention is the production and use of polyamines compound that are not metabolized to putrescine or any other naturally occurring polyamine metabolite. In addition, ideal candidates should not substitute for the normal physiological functions of polyamines such as having the ability to rescue cells from DFMO induced growth inhibition in vitro.

In another aspect of the invention, compositions containing the above described compounds and derivatives are provided. Preferably, the compositions are formulated to be suitable for pharmaceutical or agricultural use by the inclusion of appropriate carriers or excipients.

FIG. 1 is a tabular representation of a large number of polyamines A-S (25 µM) that were tested for their ability to induce antizyme frameshifting using the dual luciferase reporter assay. The percent relative frameshifting value (% RF) gives a comparison of the ability of a compound to induce frameshifting compared to 25 µM spermidine. The % RF was calculated as follows. The background percent frameshifting activity determined from the 2.5 mM DFMO negative control was subtracted from the percent frameshifting activity for all compounds including the spermidine control. The background corrected frameshifting activity of each compound was then divided by the background corrected frameshifting activity induced by 25 µM spermidine and multiplied by 100. The compounds were also evaluated for their ability to rescue cells from DFMO-induced growth inhibition by determining their rescue coefficient. The rescue coefficient represents the ratio of the cell growth, as measured by O.D., in the presence of the test compound with 2.5 mM DFMO to the growth in the presence of 2.5 mM DFMO alone. The frameshift-rescue factor (FRF) is a useful factor to compare the effectiveness of the various antizyme frameshifters by taking into account their potency for inducing frameshifting and ability to rescue cells from DFMO-induced growth inhibition. The FRF was calculated by multipling the % RF value by the inverse of the rescue coefficient.

Figure 2:
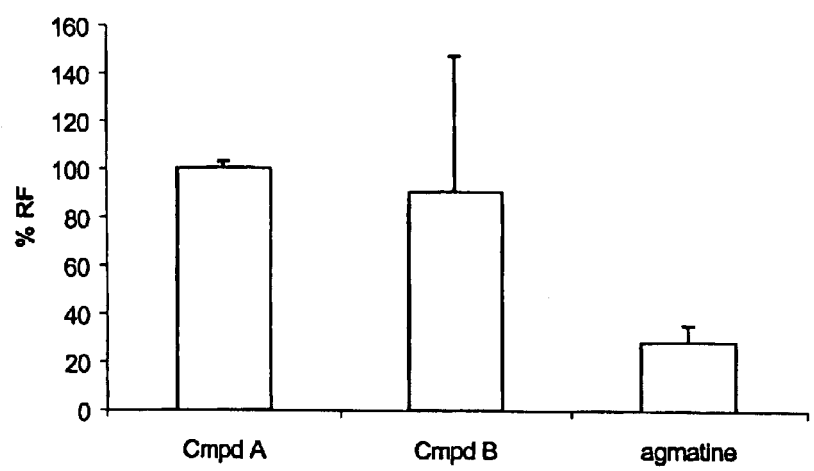
FIG. 2 shows the frameshifting induced by 25 μM of various compounds in HEK-293 cells.

FIG. 2 shows the frameshifting induced by 25 µM of various compounds in HEK-293 cells. The percent relative frameshifting (% RF) activity was determined as described above. Results are expressed as the mean ± standard deviation from these independent determinations.

Figure 3:
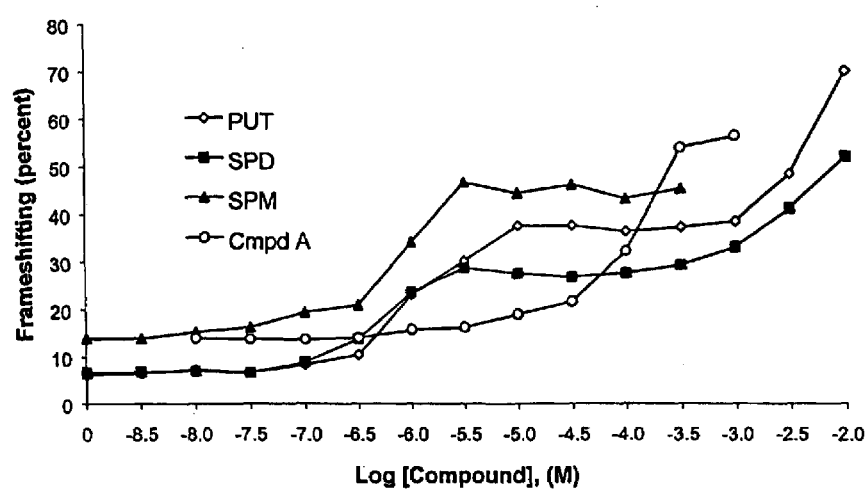
FIG. 3 shows the dose-dependent induction of frameshifting in HEK-293 cells with various compounds.

FIG. 3 shows the dose-dependent induction of frameshifting in HEK-293 cells with various compounds. Values represent percent frameshifting following transient transfection of an AZ1-IF control and the inducible 0 to +1 AZ1 plasmid construct into HEK-293 cells grown in the presence of 2.5 mM DFMO. The compounds were added to the cells after transfection and incubated overnight before assaying the next day. Each value represents triplicate measurements.

Figure 4:
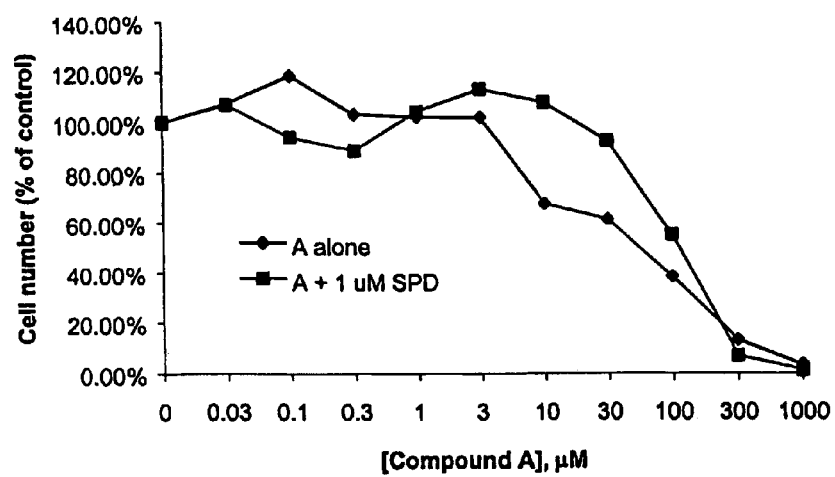
FIG. 4 shows the growth inhibition of HEK-293 cells with compound A.

FIG. 4 shows the growth inhibition of HEK-293 cells with compound A. HEK-293 cells were incubated with 1 mM aminoguanidine and various concentrations of compound A with or without 1 µM spermidine during a 6-day growth assay. Cell number was determined by MTS/PMS assay from triplicate wells.

Figure 5:
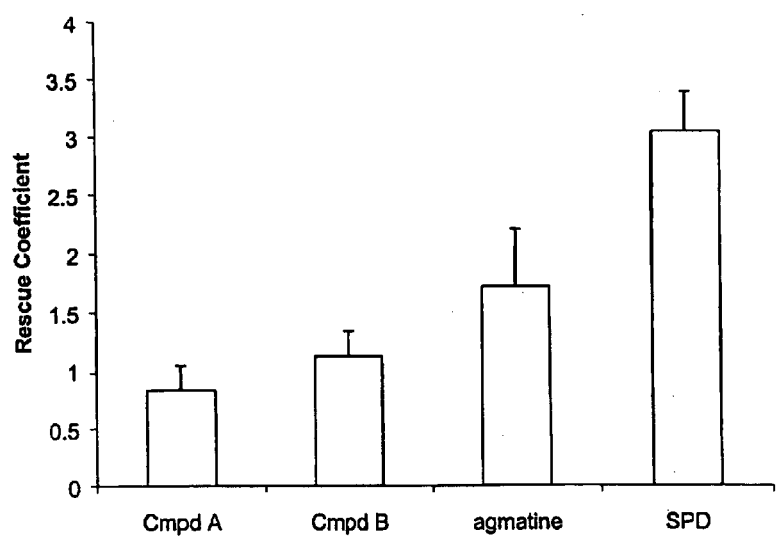
FIG. 5 gives a comparison of the ability of antizyme frameshifters (25 μM) to rescue cells from 2.5 mM DFMO-induced growth inhibition compared to 25 μM spermidine (SPD) in a 6-day assay in HEK-293 cells.

FIG. 5 gives a comparison of the ability of antizyme frameshifters (25 µM) to rescue cells from 2.5 mM DFMO-induced growth inhibition compared to 25 µM spermidine (SPD) in a 6-day assay in HEK-293 cells. The rescue coefficient represents the ratio of cell growth, as measured by O.D., of the test compound with 2.5 mM DFMO versus 2.5 mM DFMO alone.

Figure 6:
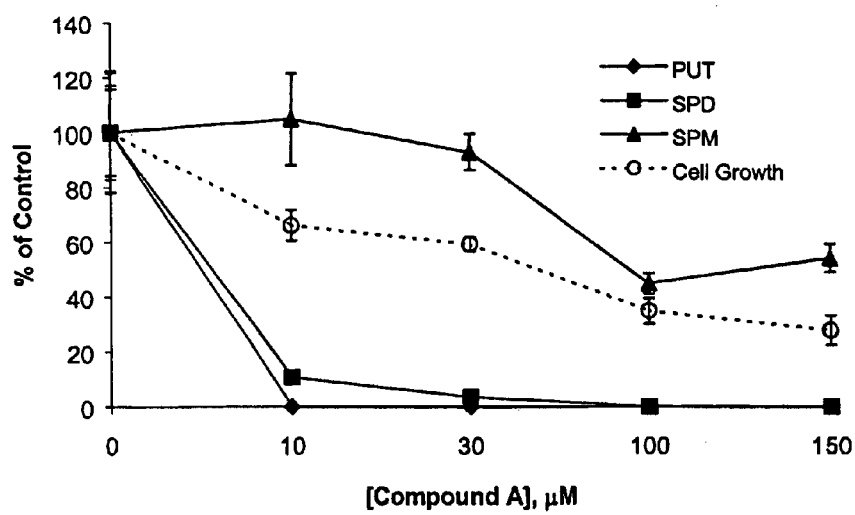
FIG. 6 is a graph showing the effect of a 6-day incubation of compound A on HEK-293 cellular polyamine levels and cell growth.

FIG. 6 is a graph showing the effect of a 6-day incubation of compound A on HEK-293 cellular polyamine levels and cell growth. All flasks received 1 mM aminoguanidine. Cells were washed, counted, lysed in perchloric acid, dansylated and polyamine levels determined by HPLC. Each value represents the average of triplicate values with the error bars representing standard deviation.

Figure 7:
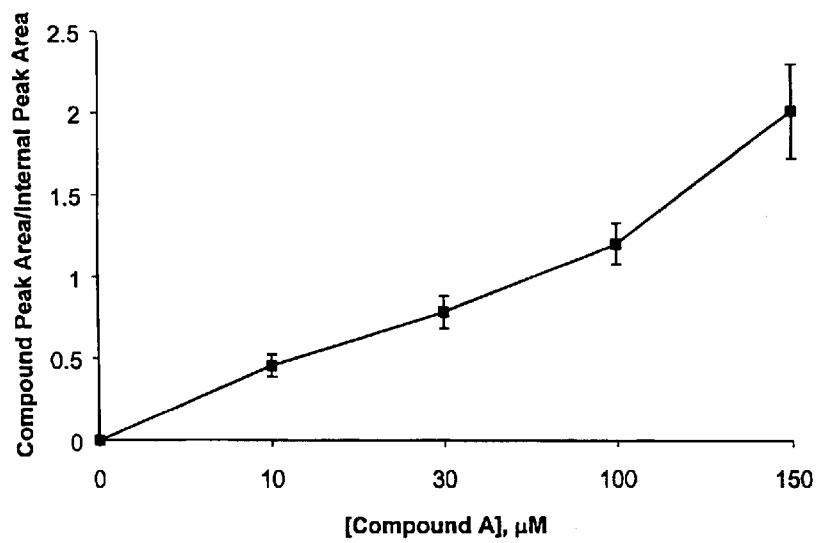
FIG. 7 illustrates the effect of extracellular compound A on the intracellular concentration of compound A in HEK-293 cells as determined by HPLC.

FIG. 7 illustrates the effect of extracellular compound A on the intracellular concentration of compound A in HEK-293 cells as determined by HPLC. Cells were prepared as in FIG. 6. Peak area was normalized by dividing the peak area of the compound divided by the peak area of the internal standard, diaminoheptane. Values represent at least triplicate measurements with the error bars representing standard deviation.

Figure 8:
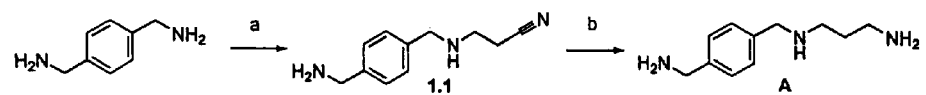
FIG. 8 shows the reaction scheme for the synthesis of compound A. Conditions and reagents: (a) $CH_2$=CHCN 1.2 equiv., $CH_3OH$ (b) $LiAlH_4$ in THF.

FIG. 8 shows the reaction scheme for the synthesis of compound A. Conditions and reagents: (a) $CH_2$=CHCN 1.2 equiv., $CH_3OH$ (b) $LiAlH_4$ in THF.

Figure 9:
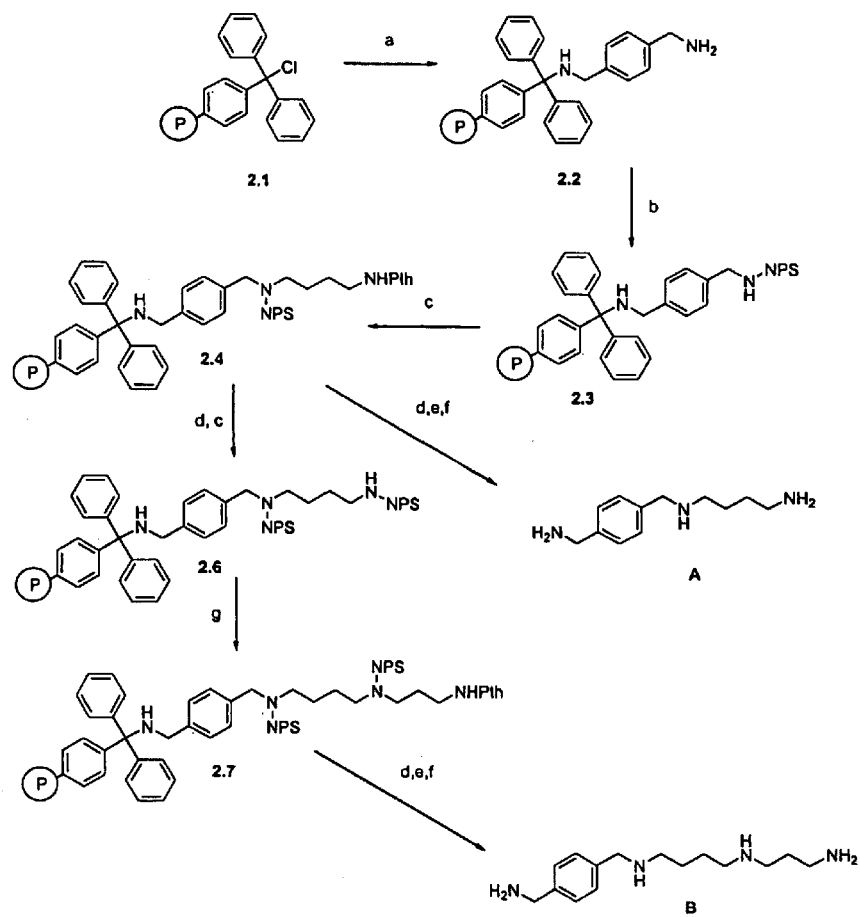
FIG. 9 shows the reaction scheme for the synthesis of compound B.

FIG. 9 shows the reaction scheme for the synthesis of compound B. Conditions and reagents: (a) p-xylylenediamine (10 equiv), $CH_2Cl_2$ (b) 2-nitrobenzenesulfonylchloride, $Et_3N$, $CH_2Cl_2$ (c) $HOCH_2CH_2CH_2CH_2NPth$, $Ph_3P$, DIAD, THF (d) $NH_2NH_2$, EtOH (e) PhSH, $K_2CO_3$, DMF (f) $TFA/CH_2CH_2/iPr_3SiH$, 20:78:2 (g) $HOCH_2CH_2CH_2NPth$, $Ph_3P$, DIAD, THF.

Figure 10:
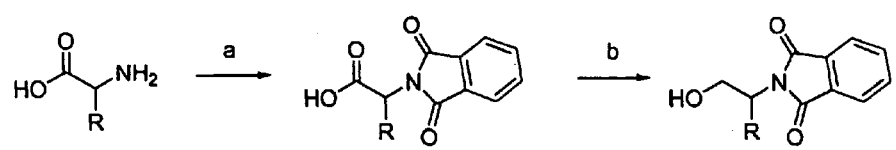
FIG. 10 shows the reaction scheme for synthesis of intermediate R groups for FIG. 11.
Figure 11:
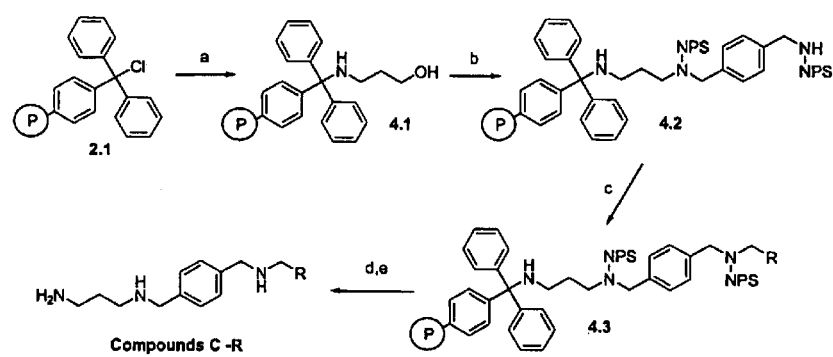
FIG. 11 shows the reaction scheme for the synthesis of compounds C—R.

FIG. 10 shows the reaction scheme for synthesis of intermediate R groups for FIG. 11. Conditions and reagents: (a) Phthalic anhydride, EtOH, reflux (b) $^tBuOCOCl$, $NaBH_4$.

FIG. 11 shows the reaction scheme for the synthesis of compounds C—R. Conditions and reagents: (a) 3-aminopropanol (10 equiv), $CH_2Cl_2$ (b) 1,4-bis-(2-nitrobenzenesulfonamide)-xylylene, $Ph_3P$, DIAD, THF (c) Intermediate 3.2, $Ph_3Ph$, DIAD, THF (d) $K_2CO_3$, PhSH, DMF (e) $TFA/CH_2CH_2/iPr_3SiH$, 20:78:2.

The following non-limiting examples are presented to further illustrate the present invention. The general procedures suitable for preparing compounds of the present invention are illustrated in the following non-limiting examples.

EXAMPLE 1

Synthesis of Compound A

N-(2-cyanoethyl)-xylylenediamine (1.1)—To the slightly cloudy solution of 6.81 g (50 mmoL) of p-xylylenediamine [539–48–0] in 250 mL of dry $CH_3OH$ is added 3.95 mL (3.18 g, 60 mmol, 1.2 equiv.) of acrylonitrile dropwise at 25° C. under an atmosphere of argon. The reaction flask is shielded from light and allowed to stir for 5 h. Thin layer chromatography ($CHCl_3$:$^iPrOH$:concd. $NH_4OH$ 80/18/2) shows a mixture of di-(2-cyanoethyl) product ($R_f$=0.63) and mono-(2-cyanoethyl) product ($R_f$=0.26) materials is formed. Only a slight trace of p-xylylenediamine ($R_f$=0.02) remains. The solvents are evaporated and the resulting oil is purified by silica gel chromatography using the following ratios of $CHCl_3$:$^iPrOH$:concd. $NH_4OH$: 85/13/2 (1 L), 80/18/2 (1 L) then 75:23:2 (1 L) to give 3.90 g (32%) of the di-(2-cyanoethyl) product as a white solid. The desired mono-(2-cyanoethyl) product eluted in later column fractions and weighs 3.06 g (32%) as a colorless oil.

N-(3-aminopropyl)-xylylenediamin (Compound A)—To the clear homogeneous solution of 1.97 g (10.4 mmole) of N-(2-cyanoethyl)-xylylenediamine in 50 mL of dry THF is added 30 mL (30 mmole) of a 1M solution of lithium aluminum hydride ($LiAlH_4$) in THF dropwise at 25° C. under an atmosphere of argon. Bubbles form and a white precipitate forms immediately. A pink color is noted. After stirring for 1 h the heterogeneous reaction mixture is placed in an oil bath and heated to reflux for 18 h. The reaction is allowed to cool and 10 mL of $H_2O$ is carefully added. This is followed by the addition of 10 mL of 4N NaOH. The resulting mixture is heated to reflux for 4 h when it is filtered over a pad of Celite after only slight cooling. The white precipitate on the Celite pad is washed twice each with $CH_3OH$, THF then $CH_2Cl_2$. The combined filtrates are evaporated to give 4.20 g oily crude product. This is purified by $SiO_2$ column chromatography using the following concentrations of concd. $NH_4OH$ in $CH_3CN$: 5% (1 L) and 20% (1 L) to give 1.52 g (76% of product as a colorless clear oil. This is dissolved in 50 mL of EtOH and treated with 10 mL of 6N HCl followed by evaporation. The resulting white solid is suspended in 50 mL of hot EtOH and treated with just enough $H_2O$ to form a complete solution. This solution is stored at −20° C. to produce the first crop of crystals that are filtered and dried to give 0.52 g (16%) pure product. The mother liquor is evaporated and treated as above with less solvent to give 0.34 g (11%) as the second crop crystals (FIG. 8).

EXAMPLE 2

Synthesis of Compound B

Resin 2.2—To a 100 mL solid-phase peptide synthesis vessel containing 10 g (Rapp Polymere, 14 mmole, 1.4 mmole/g) of polystyrene-based trityl chloride resin in 30 mL of $CH_2Cl_2$ is added a solution of 19.07 g (140 mmole, 10 equiv) of p-xylylenediamine in 30 mL of $CH_2Cl_2$ dropwise at 25° C. over 30 min. During this addition the resin is agitated via the introduction of a slow stream of argon through the bottom frit of the vessel. Copious amounts of white precipitate form over the course of the 8 h reaction. Following this time the resin is filtered and washed with $CH_2Cl_2$, $^iPrOH$, DMF, THF then $CH_2Cl_2$ (3×75 mL each). The dried resin is treated with 10 mL of diethylamine in 40 mL of $CH_2Cl_2$ for 2 h to completely cap the resin. The same washing procedure as above followed by a thorough overnight vacuum drying process takes place to give the product resin. This resin gives a positive Kaiser amine test reaction.

Resin 2.3—All of the resin from the step are suspended in 50 mL of $CH_2Cl_2$ in a 100 mL solid-phase peptide synthesis vessel and treated with 9.31 g (42 mmole, 3 equiv) of 2-nitrobenzenesulfonyl chloride and 5.85 mL (4.25 g, 42 mmole, 3 equiv) of triethylamine at 25° C. The resin is agitated via the introduction of a slow stream of argon through the bottom frit of the vessel for 4 h when the resin is filtered and washed with $CH_2Cl_2$, $^iPrOH$, DMF, THF then $CH_2Cl_2$ (3×75 mL each). The resin is dried under vacuum overnight to give a product that is negative by the Kaiser amine test reaction.

Resin 2.4—To all of the resin obtained above suspended in 30 mL of dry THF is added as solids 11.02 g (42 mmole, 3 equiv) of triphenylphosphine and 9.21 g (42 mmole, 3 equiv) of 4-phthalimide-1-butanol. The resulting suspension is agitated with a slow stream of argon through the bottom of the vessel while 8.49 g (42 mmole, 3 equiv) of diisopropylazodicarboxyate is introduced in a dropwise fashion. The resulting suspension is agitated for 18 h at 25° C. when the solvents are filtered and washed with $CH_2Cl_2$, $^iPrOH$, DMF, THF then $CH_2Cl_2$ (3×75 mL each). The resin is dried under vacuum overnight to give a product that is negative by the Kaiser amine test reaction.

Resin 2.5—To all of the resin produced above is added 50 mL of absolute EtOH and 50 mL of hydrazine hydrate in a solid-phase peptide synthesis vessel. The resulting suspension is heated to 60° C. and rotated in a Robins Scientific ChemFlex Model 404 oven. After 18 h at this temperature the vessel is allowed to cool and the resin is filtered and washed with $H_2O$, EtOH, $CH_2Cl_2$, $^iPrOH$, DMF, THF then $CH_2Cl_2$ (3×75 mL each). The resin is dried under vacuum overnight to give a product that is positive by the Kaiser amine test reaction.

Resin 2.6—Resin 2.5 is treated in a similar manner as that described for resin 2.3 above to give resin 2.6 as product. The resin is dried under vacuum overnight to give a product that is negative by the Kaiser amine test reaction.

Resin 2.7—To all of the resin 2.6 obtained above suspended in 30 mL of dry THF is added as solids 11.02 g (42 mmole, 3 equiv) of triphenylphosphine and 8.62 g (42 mmole, 3 equiv) of N-(3-hydroxypropyl)phthalimide. The resulting suspension is agitated with a slow stream of argon through the bottom of the vessel while 8.49 g (42 mmole, 3 equiv) of diisopropylazodicarboxyate is introduced in a dropwise fashion. The resulting suspension is agitated for 18 h at 25° C. when the solvents are filtered and washed with $CH_2Cl_2$, $^iPrOH$, DMF, THF then $CH_2Cl_2$ (3×75 mL each). The resin is dried under vacuum overnight to give a product that is negative by the Kaiser amine test reaction.

N-(4-amino-1-butane-N-(3-aminopropyl-)-xylylenediamine (Compound B)—One gram of Resin 2.7 obtained above is treated with 10 mL each of EtOH and hydrazine hydrate at 60° C. for 18 as above for Resin 2.5. After 18 h at this temperature the vessel is allowed to cool and the resin is filtered and washed with $H_2O$, EtOH, $CH_2Cl_2$, $^iPrOH$, DMF, THF then $CH_2Cl_2$ (3×75 mL each). The resin is dried under vacuum overnight to give a product that is positive by the Kaiser amine test reaction. The resulting resin is treated with 1.74 g (12.6 mmole, 9 equiv) of $K_2CO_3$ and 1.29 mL (12.6 mmole, 9 equiv) of thiophenol in 10 mL of dry DMF at 25° C. for 3 h. The resin is filtered and washed with $CH_2Cl_2$, $^iPrOH$, DMF, THF then $CH_2Cl_2$ (3×15 mL each) to give a product that gave a positive Kaiser amine test reaction. This resin is suspended in 10 mL of TFA/$CH_2Cl_2$/$^iPr_3SiH$ 20:78:2 and agitated for 30 min. on a platform shaker. The resin is filtered and washed 3 times with 20 mL of $CH_2Cl_2$ then 3 times with $CH_3OH$. The combined filtrates are evaporated to give compound B as its crude tetratrifluoroacetate salt. This could be purified over silica gel using a 5 to 40% gradient of concd $NH_4OH$ in $CH_3CN$ using a fraction collector. The resulting fractions are analyzed by TLC ($R_f$=0.34 in 70:30 $CH_3CN$/concd $NH_4OH$) and those containing pure product are combined and evaporated to give pure Compound B as a clear oil. This is totally converted to its tetrahydrochloride salt by dissolving in 20 mL of $CH_3OH$ and treating with an excess of 6N HCl. Evaporation of the solvents gives 149 mg (26%) white solid (FIG. 9).

Resin precursor to Compounds C through R (Resin 4.2)—To a 100 mL solid-phase peptide synthesis vessel containing 10 g (Rapp Polymer 14 mmole, 1.4 mmole/g) of polystyrene-based trityl chloride resin in 30 mL $CH_2Cl_2$ is added a solution of 10.51 g (140 mmole, 10 equiv) of 3-aminopropanol in 30 mL of $CH_2Cl_2$ dropwise at 25° C. over 30 min. During this addition the resin is agitated via the introduction of a slow stream of argon through the bottom frit of the vessel. The reaction is allowed to proceed for 5 h. Following this time the resin is filtered and washed with $CH_2Cl_2$, $^iPrOH$, DMF, THF then $CH_2Cl_2$ (3×75 mL each). The dried resin is treated with 10 mL of diethylamine in 40 mL of $CH_2Cl_2$ for 2 h toied resin is treated with 10 mL of diethylamine in 40 mL of $CH_2Cl_2$ for 2 h to completely cap the resin. The same washing procedure as above followed by a thorough overnight vacuum drying process take place to give the product resin. This resin gives a negative Kaiser amine test reaction.

1,4-bis-(2-nitrobenzenesulfonamide)-xylylene—To 13.62 g (100 mmole) of 1,4-xylylenediamine in 120 mL of dry pyridine in an ice bath under a stream of argon is added 48.76 g (220 mmole) of 2-nitrobenzenesulfonylchloride portionwise as a solid. The reaction is allowed to warm to room temperature and stir for 18 hr. A large portion of the pyridine is removed by rotoevaporation and the oily residue is dissolved in 250 mL of $CH_2Cl_2$ and washed with satd $CuSO_4$ then $H_2O$ and brine. Drying and evaporation gives a crude product as a yellowish solid. Purification by silica gel column chromatography using $CHCl_3/CH_3OH$ 98:2 gives 39.5 g (78%) of product as a white solid.

Resin 4.2—To 2 g of Resin 4.1 produced above is added 4.2 g (3 equiv) of 1,4-bis-(2-nitrobenzenesulfonamide)-xylylene and 2.20 g (3 equiv) of triphenylphosphine in 20 mL of dry THF. To the resulting suspension is added 1.65 g of diisopropyl-azodicarboxylate dropwise at room temperature over 45 min. The resin is agitated over the next 18 h by the introduction of a slow stream of argon through the bottom frit of the vessel. After this time the resin is filtered and washed with $CH_2Cl_2$, $^iPrOH$, DMF, THF then $CH_2Cl_2$ (3×25 mL each). The resin gives a negative Kaiser amine test.

EXAMPLE 3

Synthesis of Compound C

Resin 4.3—To 0.5 g of Resin 4.2 and 0.55 g (3 equiv) of triphenylphosphine suspended in 10 mL of dry THF is added 0.43 g of 2-methyl-2-phthalimido-1-ethanol produced via the route shown in FIG. 10 (other compounds in FIG. 1 are produced by use of the appropriate precursor molecule). To the resulting suspension is added 0.42 g of diisopropyl-azodicarboxylate dropwise at room temperature over 45 min. The resin is agitated over the next 18 h by the introduction of a slow stream of argon through the bottom frit of the vessel. After this time the resin is filtered and washed with $CH_2Cl_2$, $^iPrOH$, DMF, THF then $CH_2Cl_2$ (3×25 mL each). The resin gives a negative Kaiser amine test.

N-(3-aminopropyl)-N'-(2-methyl-2-aminoethyl)-1,4-xylylenediamine (Compound C)—To a 0.25 gram portion of Resin 4.2 obtained above is added 10 mL each of EtOH and hydrazine hydrate. The resin is heated at 60° C. for 18 as for Resin 2.5 above. After 18 h at this temperature the vessel is allowed to cool and the resin is filtered and washed with $H_2O$, EtOH, $CH_2Cl_2$, $^iPrOH$, DMF, THF then $CH_2Cl_2$ (3×75 mL each). The resin is dried under vacuum overnight to give a product that is positive by the Kaiser amine test reaction. The resulting resin is treated with 0.435 g (3.15 mmole, 9 equiv) of $K_2CO_3$ and 0.32 mL (3.15 mmole, 9 equiv) of thiophenol in 10 mL of dry DMF at 25° C. for 3 h. The resin is filtered and washed with $CH_2Cl_2$, $^iPrOH$, DMF, THF then $CH_2Cl_2$ (3×15 mL each) to gives a product that gives a positive Kaiser amine test reaction. This resin is then suspended in 10 mL of $TFA/CH_2Cl_2/^iPr_3SiH$ 20:78:2 and agitated for 30 min. on a platform shaker. The resin is filtered and washed 3 times with 20 mL of $CH_2Cl_2$ then 3 times with $CH_3OH$. The combined filtrates are evaporated to give compound C as its crude tetra-trifluoroacetate salt. This could be purified over silica gel using a 5 to 40% gradient of concd $NH_4OH$ in $CH_3CN$ using a fraction collector. The resulting fractions are analyzed by TLC ($R_f$=0.18 in 70:30 $CH_3CN$/concd $NH_4OH$) and those containing pure product are combined and evaporated to give pure compound C as a clear oil in its free base form. This is totally converted to its tetrahydrochloride salt by dissolving in 20 mL of $CH_3OH$ and treating with an excess of 6N HCl. Evaporation of the solvents gives 30 mg (22%) white solid (FIG. 11).

EXAMPLE 4

Cell Culture and Reagents

All cell lines are obtained from ATCC (Manassas, Va.) and cultured in the recommended media, serum, and $CO_2$ concentration. Medias are obtained from Mediatech, Inc. (Hermdon, Wash.) and serums from Gibco BRL (Gaithersburg, Md.). 50 U/mL penicillin, 50 mg/mL streptomycin and 2 mM L-glutamine (all from BioWhittaker, Walkersville, Md.) are included in all cultures. When cells are cultured with polyamines or polyamine analogs, 1 mM aminoguanidine (AG; Sigma) is included to inhibit serum amine oxidase activity. DFMO is obtained from Advanced ChemTech (Louisville, Ky.).

EXAMPLE 5

Polyamine Analogs Induce Antizyme Frameshifting

A series of compounds are screened for their ability to induce frameshifting using the dual luciferase reporter assay. HEK-293 cells are plated in white sided, clear-bottomed 96-well assay plates at 15,000 cells per well in 100 µL of medium (DMEM supplemented with 10% fetal bovine serum (Gibco), 1% penicillin, streptomycin and L-glutamine) containing 2.5 mM DFMO. The cells are incubated for 2-days at 37° C. in an atmosphere of 5% $CO_2$. The medium is removed and the cells are then transfected with lipofectamine reagent (LifeTechnologies) using serum free DMEM. All cells are transfected overnight with 100 ng of the appropriate plasmid DNA and 0.3 µL lipofectamine in 50 µL of serum free DMEM containing 2.5 mM DFMO. The next day, 40 µL of medium is added per well containing 3.1 mM DFMO, 2.5 mM aminoguanidine and 25% FBS. Compounds are diluted in either water or medium to 0.25 mM and 10 µL is added per well such that the final concentration is 25 µM. The positive control contains 25 µM spermidine and for the negative control no compound is added. The cells are incubated overnight at 37° C. in an atmosphere of 5% $CO_2$, washed once with 1×PBS, lysed with 50 µL of passive lysis buffer (Promega) and assayed for renilla and firefly luciferase activity using the Dual-Luciferase Reporter Assay System (Promega). The percent frameshifting activity is determined by dividing the ratio of the firefly luciferase to renilla luciferase activity in cells transfected with the inducible 0 to +1 Az1 construct by the ratio of the firefly luciferase to renilla luciferase activity in cells transfected with the control vector AZ-IF and multiplied by 100.

The percent relative frameshifting value (% RF) gives a comparison of the ability of a compound to induce frameshifting compared to 25 µM spermidine. The % RF is calculated as follows. The background percent frameshifting activity determined from the 2.5 mM DFMO negative control is subtracted from the percent frameshifting activity for all compounds including the spermidine control. The background corrected frameshifting activity of each compound is then divided by the background corrected frameshifting activity induced by 25 µM spermidine and multiplied by 100.

From the above screenings, a number of compounds are found to induce frameshifting (FIG. 1 and FIG. 2). Some of these compounds induce frameshifting substantially better than spermidine at the same concentration (25 µM). To determine the potency for inducing antizyme frameshifting, the polyamines spermine, spermidine, putrescine and compound A are also titrated using the dual luciferase reporter assay (FIG. 3). $EC_{50}$ represents the concentration of the compound that resulted in 50% of the maximum percent frameshifting as measured by the plateau values in FIG. 3. The titration indicates that $EC_{50}$ values for induction of frameshifting of all three polyamines are close to 1 µM with a rank order potency of spermidine (0.56 µM)>spermine (0.68 µM)>putrescine (0.95 µM). Compound A has a less potent $EC_{50}$ for frameshifting of about 120 µM. The maximum levels of frameshifting also vary between putrescine, spermidine, spermine and compound A.

It has generally been reported that the rank order potency for frameshift induction by the polyamines beginning with the most potent is spermine, followed by spermidine then putrescine. However in this study (FIG. 3), the polyamines all have a similar potency with $EC_{50}$ values between 0.5–1.0 µM. Spermine has been reported to have a similar value (Mitchell, J. L. A. et. al., *Biochem. J.* Vol. 366, p.663–671, 2002). In the cell-based assay, both putrescine and spermidine can be converted intracellularly into spermidine and spermine via the transfer of an aminopropyl group by spermidine synthase or spermine synthase, respectively. It is conceivable the frameshifting activities observed for putrescine and spermidine may actually reflect a combination of activities for the polyamines synthesized during the course of the assay.

EXAMPLE 6

Growth Inhibition Assay

Cells are plated in 96-well plates such that they would be in log growth for the duration of the assay. The day after plating, the polyamine analogs are added to the cells, and growth, if any, permitted to continue for six days in the presence of 1 mM AG and 1 µM SPD when appropriate. At the end of six days, cell growth is measured by MTS/PMS dye assay (Cell Titer 96 Aqueous Non-Radioactive Cell Proliferation Assay; Promega, Madison, Wis.). $IC_{50}$ refers to the concentration of the polyamine analog that results in 50% of maximum cell growth inhibition.

The cell growth of HEK-293 cells is inhibited by compound A (FIG. 4). An $IC_{50}$ of approximately 60 µM is found for growth inhibition with this polyamine analog. Addition of 1 µM spermidine did rescue the cells from this growth inhibition between 3–100 µM of compound A (FIG. 4). These results suggest that spermidine competes with compound A for entry into the cell and that compound A enters the cell at least in part through the polyamine transporter.

EXAMPLE 7

Polyamine Analogs and Rescue From DFMO Induced Growth Inhibition

Compounds found to induce antizyme frameshifting are evaluated for the undesired ability to rescue cells from DFMO-induced growth inhibition (FIG. 1 and FIG. 5). HEK-293 cells are plated in 96-well assay plates at 1,000 cells per well in 100 µL of medium (DMEM supplemented with 10% fetal bovine serum (Gibco), 1% penicillin, streptomycin and L-glutamine). The cells are incubated overnight at 37° C. in an atmosphere of 5% $CO_2$. Compounds are added the next day to a final concentration of 25 µM along with 1 mM aminoguanidine (inhibits serum amine oxidase) and 2.5 mM DFMO in a final volume of 200 µL medium. The positive control contained 25 µM spermidine. The cells are allowed to incubate for 6 days before cell growth is measured by MTS/PMS dye assay (Cell Titer 96 Aqueous Non-Radioactive Cell Proliferation Assay, Promega). The rescue coefficients in FIG. 1 and FIG. 5 are expressed as the ratio of the O.D. ((compound+2.5 mM DFMO)/O.D. (2.5 mM DFMO alone)). Therefore, DFMO alone has a value of one. If the drug has the desired effect of no rescue then it has a value close to DFMO alone (i.e. about 1). If the value is less than one, then the compound is growth inhibitory. If the value is 0, the compound is cytotoxic. Compounds that rescued cells from DFMO induced growth inhibition give ratios higher than one and are less desirable as therapeutics.

As shown in FIG. 5, neither compound A nor B significantly rescue cells from DFMO-induced growth inhibition. Compound A is the least effective in comparison to the spermidine control. Agmatine is somewhat better than either A or B in rescuing cells from DFMO induced growth inhibition.

A useful factor to compare the effectiveness of the various antizyme frameshifters takes into account their potency for inducing frameshifting and inability to rescue cells from DFMO-induced growth inhibition. This measure is referred to as the frameshift-rescue factor (FRF). The FRF is calculated by multiplying the % RF value by the inverse of the rescue coefficient. This method greatly increases the simplicity of analyzing multiple data parameters. If either the % RF value is low or the rescue coefficient high, the compound does not stand out as a potential candidate. Using this analysis with compounds A, B and agmatine, FRF values of 120, 83 and 17 are obtained, respectively. Based on this method of analysis, compound A potentially has the greatest ability to deplete polyamine levels and inhibit cell growth.

EXAMPLE 8

Depletion of Intracellular Polyamine Levels with Compound A

Compound A is further evaluated to determine if it depletes intracellular polyamine levels in HEK-293 cells in a dose-dependent fashion (FIG. 6). HEK-293 cells are plated in 75 cm² flasks at 300,000 cells/mL to insure they would be in log growth for the duration of the experiment. After overnight incubation at 37° C. in an atmosphere of 5% $CO_2$, compound A is added along with 1 mM aminoguanidine. The flasks are then incubated for 6 days at 37° C. in an atmosphere of 5% $CO_2$. The cells are harvested by washing twice with ice-cold 1×PBS, trypsinized, counted, and lysed in 0.4 N perchloric acid. Diaminoheptane is used in all dansylation reactions as an internal standard. Peak area is normalized by dividing the peak area of the compound divided by the peak area of the internal standard. The HPLC method for the fluorometric detection of polyamines from the cell extracts is based on the procedure by Kabra (Kabra, P. M. et. al. *J. Chromatogr.* 380:19–32 (1986)).

It is expected that if compound A induces frameshifting and therefore elevates the level of antizyme, intracellular levels of polyamines would decrease. This is observed in HEK-293 cells, which show significant reductions of intracellular levels of polyamines (FIG. 6). Putrescine is most sensitive to the treatment and is non-detectable at the lowest concentration tested. Spemidine levels are down by about 90% at 10 µM and are non-detectable when incubated with 100 μM of compound A. Cell growth is also affected, decreasing by 32% at 10 μM and 38.5% at 30 μM. Spermine levels initially remained steady as has been generally found for many polyamine depletion therapies involving ODC inhibition. However, spermine levels are reduced by 50% at 100 μM. The intracellular levels of compound A also increase dose-dependently (FIG. 7).

Cell growth inhibition positively correlates with the decreasing polyamine levels (FIG. 6). The huge drop in the intracellular levels of putrescine and spermidine may lead to the initial inhibition of cell growth. At compound A levels above 30 μM, spermine levels also begin to diminish to approximately 50% of normal. It is possible that if spermine levels fall below 50% of normal then cell death will occur. This is supported by the fact that although the intracellular spermine concentration levels off at about 50% of normal, cell growth continues to diminish. Perhaps as the extracellular levels of Compound A increase, fewer cells are able to maintain intracellular spermine levels at the critical level of 50% of normal. The evidence for the 50% threshold level arises from the fact that only those cells that are living (still attached to the plate) are harvested and their intracellular polyamine levels determined. Presumably, the dead cells expire because their spermine levels fell below 50%.

EXAMPLE 9

Potency of Polyamine Analogs Versus Agmatine

Agmatine is an additional compound reported to induce antizyme frameshifting (Satriano, J. et. al., *J. Biol. Chem.* 273:15313–15316 (1998)). It has a reported maximum frameshifting efficiency at 4 mM. It is also found to inhibit mouse kidney proximal tubule (MCT) cell proliferation with maximum growth inhibition observed by 1 mM. Studies at MediQuest Therapeutics have found that agmatine inhibits growth with an $IC_{50}$ of approximately 2 mM in MDA-MB-231 cells, 5 mM in the prostate PC-3 cells line and 0.21 mM in HEK-293 cells (data not shown). Both compound A and B are found to be more potent than agmatine in inducing antizyme frameshifting (FIG. 2). Compound A is also a more potent inhibitor of HEK-293 cell growth with an $IC_{50}$ of 60 μM and is cytotoxic at 1 mM. It has been previously shown that forced expression of antizyme can result in cell death. The toxicity of compound A observed at 1 mM suggests that a potent antizyme inducer can be cytotoxic when the antizyme levels reach a sufficiently high threshold value.

EXAMPLE 10

Polyamine Analogs that Inhibit Polyamine Transport and Induce Antizyme Frameshifting A number of compounds have been developed in recent years that inhibit polyamine transport (Huber, M. et. al., *J. Biol. Chem.* 271:27556–27563 (1996); Covassin, L. et. al., *Bioorg. Med. Chem. Lett.* 9:1709–1714 (1999); Zhang, M. et. al., *J. Mol. Med.* 5:595–605 (1999); Aziz, S. M. et al *J. Pharmacol. Exp. Ther.* 274:181–186 (1995); Tomasi, S. et. al., *Bioorg. Med. Chem. Lett.* 8:635–640 (1998); Cullis, P. M. et. al., *Chem. Biol.* 6:717–729 (1999); Chao, J. et. al., *Mol. Pharmacol.* 51:861–871 (1997); Weeks, R. S. et. al., *Exp. Cell. Res.* 261:293–302 (2000); Burns, M. R. et. al., *J. Med. Chem.* 44:36232–3644 (2001); Graminski, G. F. et. al., *Bioorg. Med. Chem. Lett.* 12:35–40 (2002)). These compounds are generally thought to bind to the transporter but are not in themselves substrates for the transporter. It is conceivable that a number of these reported transport inhibitors may inhibit the transporter indirectly by activating antizyme. For example, Poulin has described potent transport inhibitors that crosslink sym-norspermidine via its secondary amino groups with compounds such as a planar p-xylyl crosslinker (Covassin, L. et. al., *Bioorg. Med. Chem. Lett.* 9:1709–1714 (1999)). The 1,4-bis[bis(3-aminopropyl)] xylene diamine analog (Compound S) has been found to induce antizyme frameshifting using the dual luciferase reporter assay. At a concentration of 25 μM, this compound is found to induce frameshifting with a % RF of 100. When tested for its ability to rescue from 2.5 mM DFMO induced growth inhibition, it shows no ability to rescue at 25 μM (FIG. 1). These results suggest that 1,4-bis[bis(3-aminopropyl)xylene diamine can enter the cell and inhibit transport at least in part through induction of full length antizyme.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this invention can be administered by any conventional method available for use in conjunction with pharmaceuticals, either as individual therapeutic agents or in a combination of therapeutic agents.

The dosage administered well, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5–95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238–250 (1982) and *ASHP Handbook on Injectable Drugs*, Toissel, 4th ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthishes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present invention should be sufficient to effect a therapeutic response in the animal over a reasonable time frame. One skilled in the art will recognize that dosage will depend upon a variety of factors including a condition of the animal, the body weight of the animal, as well as the condition being treated.

A suitable dose is that which will result in a concentration of the active agent in a patient which is known to effect the desired response.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present invention can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are ished and dried. The active ingredient can be dissolved in a mixture of polyethylene glycol, glycerin and sorbitol to prepare a water miscible medicine mix.

Tablets

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A polyamine having the structure

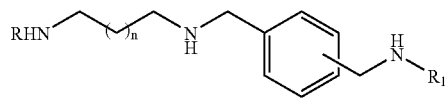

wherein, n can be 0 to 8 and the aminomethyl functionality can be ortho, meta or para substituted, R is hydrogen, 2-aminoethyl, 3-aminopropyl, 4-aminobutyl, 5-aminopentyl, 6-aminohexyl, 7-aminoheptyl, or 8-aminooctyl and $R_1$ is hydrogen and wherein said polyanilne is non-symmetrical.

2. A polyamine selected from the group consisting of one of the following compounds:

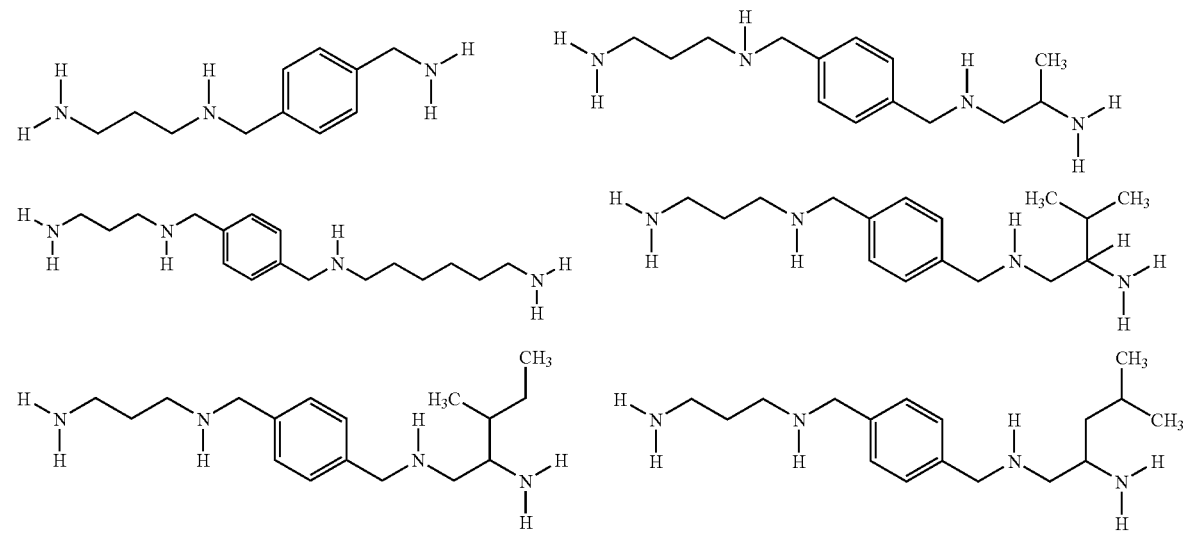

-continued

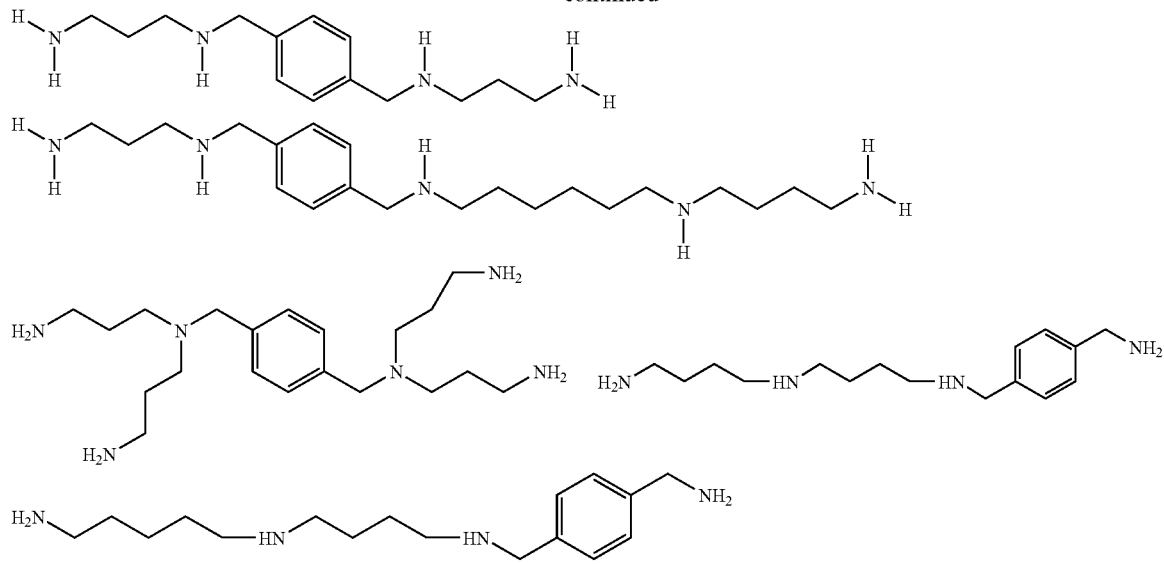

3. A pharmaceutical composition comprising a polyamine according to any one of claims 1 or 2 and a pharmaceutically acceptable excipient, diluent or vehicle.

4. The composition of claim 3 wherein said excipient, diluent or vehicle is pharmaceutically acceptable.

5. The composition of claim 3 wherein said excipient, diluent or vehicle is for topical or intra-aural administration.

6. The composition of claim 3 formulated for intravenous, subcutaneous, intramuscular, intracranial, intraperitoneal, topical, transdermal, intravaginal, intranasal, intrabronchial, intracranial, intraocular, intraaural, rectal, or parenteral administration.

7. The polyamine of claim 1 wherein said structure is

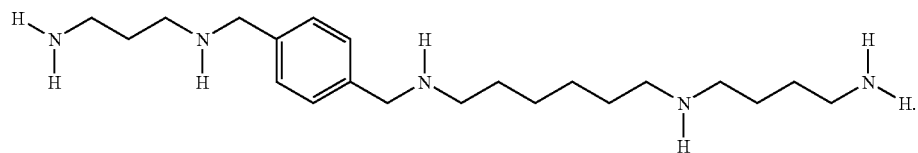

8. The polyamine of claim 1 wherein is

9. The polyamine of claim 1 wherein said structure is

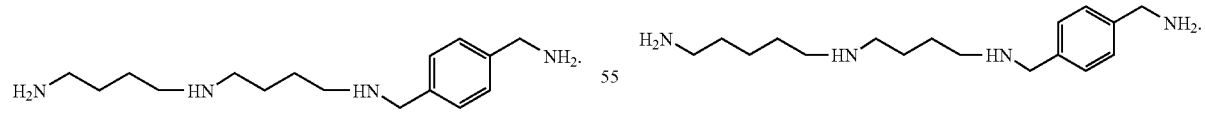

* * * * *